United States Patent
Bagheri et al.

(10) Patent No.: US 11,796,543 B2
(45) Date of Patent: Oct. 24, 2023

(54) COLORIMETRIC SYSTEM FOR DETECTION OF COVID-19 USING SALIVARY METABOLITES

(71) Applicants: Hasan Bagheri, Tehran (IR); Mohammad Mahdi Bordbar, Fasa (IR); Hosein Khoshsafar, Tehran (IR); Pegah Hashemi, Tehran (IR); Mostafa Ghanei, Tehran (IR)

(72) Inventors: Hasan Bagheri, Tehran (IR); Mohammad Mahdi Bordbar, Fasa (IR); Hosein Khoshsafar, Tehran (IR); Pegah Hashemi, Tehran (IR); Mostafa Ghanei, Tehran (IR)

(73) Assignee: FARIN BEHBOOD TASHKHIS COMPANY, Tehran (IR)

( * ) Notice: Subject to any disclaimer, the term of this patent is extended or adjusted under 35 U.S.C. 154(b) by 0 days.

(21) Appl. No.: 17/850,066

(22) Filed: Jun. 27, 2022

(65) Prior Publication Data

US 2022/0334114 A1 Oct. 20, 2022

Related U.S. Application Data

(60) Provisional application No. 63/307,164, filed on Feb. 7, 2022.

(51) Int. Cl.
*G01N 21/78* (2006.01)
*G01N 33/569* (2006.01)

(52) U.S. Cl.
CPC ....... *G01N 33/56983* (2013.01); *G01N 21/78* (2013.01)

(58) Field of Classification Search
CPC .. G01N 33/56983; G01N 21/78; G01N 21/80; G01N 2021/7793; B01L 3/5055
See application file for complete search history.

(56) References Cited

U.S. PATENT DOCUMENTS

| 2003/0059947 A1* | 3/2003 | Takagi | G01N 33/84 436/163 |
| 2004/0012789 A1* | 1/2004 | Guthermann | G01N 21/49 356/446 |

(Continued)

FOREIGN PATENT DOCUMENTS

| CN | 109239058 A | * | 1/2019 | G01N 21/25 |
| CN | 112268899 A | * | 1/2021 | G01N 21/78 |

(Continued)

OTHER PUBLICATIONS

Huanan Guan et al. Real-time visualization of colorimetric probe for pH-sensitive based on poly-(γ-glutamic acid)-functionalized gold nanoparticles (Apr. 20, 2014), ScienceDirect, vol. 448 (Year: 2014).*

(Continued)

*Primary Examiner* — Matthew D Krcha
*Assistant Examiner* — Sophia Y Lyle
(74) *Attorney, Agent, or Firm* — Bajwa IP Law Firm; Haris Zaheer Bajwa

(57) ABSTRACT

A system for detecting COVID-19 infection, including a colorimetric sensor, an image-capturing device, and a processing unit connected to the image-capturing device. The colorimetric sensor includes an injection zone and a detection zone patterned on a paper, where the injection zone covers the detection zone by folding the paper. The injection zone is configured to inject a saliva sample acquired from a person thereon. The detection zone includes an array of chemical receptors configured to interact with the injected saliva penetrating into the detection zone. The processing unit is configured to perform a method of capturing a first image from the detection zone before injection of the saliva sample, capturing a second image from the detection zone after injection of the saliva sample, and detecting COVID-19 infection status of the person by analyzing color changes (Continued)

of the array of chemical receptors in the second image respective to the first image.

11 Claims, 18 Drawing Sheets

(56) References Cited

U.S. PATENT DOCUMENTS

| | | | |
|---|---|---|---|
| 2005/0266574 A1* | 12/2005 | Kosaka | G01N 33/70 |
| | | | 436/86 |
| 2010/0166604 A1* | 7/2010 | Lim | G01N 31/22 |
| | | | 977/773 |
| 2012/0086942 A1* | 4/2012 | Honda | G01N 21/31 |
| | | | 356/436 |
| 2021/0302436 A1* | 9/2021 | Rai | G01N 21/6428 |
| 2021/0349104 A1* | 11/2021 | Wohlstadter | G01N 33/56983 |
| 2021/0364536 A1* | 11/2021 | Busa | G01N 21/274 |

FOREIGN PATENT DOCUMENTS

| | | | | |
|---|---|---|---|---|
| CN | 109239058 B | * | 1/2022 | G01N 21/25 |
| WO | WO-2016082003 A1 | * | 6/2016 | |

OTHER PUBLICATIONS

Yixuan Pan et al. Rapid discrimination of commercial American ginseng and Asian ginseng according to diols composition using a colorimetric sensor array (Sep. 1, 2019), ScienceDirect, vol. 294 (Year: 2019).*

Liu Y, Cao F, Xiong H, Shen Y, Wang M (2016) Application of 2,4-Dinitrophenylhydrazine (DNPH) in High-Throughput Screening for Microorganism Mutants Accumulating 9α-Hydroxyandrost-4-ene-3,17-dione (9α-OH-AD). PLoS ONE 11(10): e0163836. https://doi.org/10.1371/journal.pone.0163836 (Year: 2016).*

* cited by examiner

704

COLORIMETRIC SYSTEM FOR DETECTION OF COVID-19 USING SALIVARY METABOLITES

CROSS-REFERENCE TO RELATED APPLICATION

This application claims the benefit of priority from pending U.S. Provisional Patent Application Ser. No. 63/307,164 filed on Feb. 7, 2022, and entitled "A METHOD FOR RAPID DETECTION OF COVID-19 USING SALIVARY METABOLITES", which is incorporated herein by reference in its entirety.

TECHNICAL FIELD

The present disclosure generally relates to detection of a disease based on a saliva sample using a colorimetric sensor, and particularly, to a method and device for detection of COVID-19 infection utilizing a colorimetric sensor with an array of chemical receptors interactive with chemical markers of COVID-19 infection in a saliva sample.

BACKGROUND

As the most available fluid in human body, saliva has been used to diagnose various diseases such as autoimmune, cardiovascular, diabetic, cancerous and renal diseases as well as genetic disorders, and viral, bacterial, and fungal infections. Since saliva collection is a simple, cost-effective, and non-invasive procedure with an ability to detect virus RNA in oropharyngeal cavity, it has attracted attention of researchers for detection of COVID-19 disease. Conventionally, analysis of viral genetic materials is performed by real-time reverse-transcriptase polymerase-chain-reaction (rRT-PCR) gold standard method. Although this method provides highly valuable information, false negative responses might be obtained in some cases due to PCR limiting factors and/or sequence changes during PCR test.

Screening of chemical markers in body fluids is a simple and effective way for disease diagnosis. In fact, chemical markers are small-sized organic compounds, cations and anions, whose concentrations change by body's immune mechanism against a natural or pathological biological process. Markers of various tissues are transferred from bloodstream to saliva through intracellular or paracellular diffusion. These chemicals are characterized by spectroscopy, nuclear magnetic resonance, and chromatography methods; allowing for evaluation of concentration of one or more specific materials and for discrimination between two different saliva compositions. Accordingly, instrumental methods, utilizing chemical markers, provide a fingerprint response for each sample with detailed information on type and concentration of constituent compounds in a sample. However, such methods are considered non-user-friendly assays due to device complexity, high price, need of certain laboratory conditions, skilled technicians, and long-term tests. On the other hand, sensory devices with one or more sensing components in their structure monitor chemical markers by chemical or biological receptors, and interact with a particular analyte or a wide range of compounds, leading to electrical and optical changes. Despite high sensitivity and selectivity of bioreceptors, preparation, storage conditions, and fabrication of sensors based on these materials are not cost-effective.

There is, therefore, a need for a rapid, simple, accurate, and cost-effective sensing procedure for detecting COVID-19 infection by analyzing saliva compositions of a person suspected to be infected by COVID-19 virus.

SUMMARY

This summary is intended to provide an overview of the subject matter of the present disclosure, and is not intended to identify essential elements or key elements of the subject matter, nor is it intended to be used to determine the scope of the claimed embodiments. The proper scope of the present disclosure may be ascertained from the claims set forth below in view of the detailed description below and the drawings.

In one general aspect, the present disclosure describes an exemplary system for detecting COVID-19 infection. The system may include a colorimetric sensor, an image-capturing device, and a processing unit. In an exemplary embodiment, the colorimetric sensor may include a detection zone, an injection zone, and a hydrophobic barrier. In an exemplary embodiment, the detection zone may include an array of chemical receptors deposited on a respective array of individual areas of a hydrophilic paper. In an exemplary embodiment, the array of chemical receptors may be configured to interact with a saliva sample acquired from a person. In an exemplary embodiment, the person may be suspected to be infected by COVID-19 virus. In an exemplary embodiment, the injection zone may be configured to inject the saliva sample thereon. In an exemplary embodiment, the injection zone may include a bare part of the hydrophilic paper covering the array of chemical receptors by folding the hydrophilic paper along a line between the injection zone and detection zone. In an exemplary embodiment, the injected saliva sample may penetrate from the injection zone to the array of chemical receptors. In an exemplary embodiment, the hydrophobic barrier may include a hydrophobic material filled within texture of the hydrophilic paper except the injection zone and the array of individual areas. In an exemplary embodiment, the hydrophobic barrier may be configured to prevent spillover of the saliva sample from a first individual area of the array of individual areas to a second individual area of the array of individual areas. In an exemplary embodiment, the image-capturing device may be configured to capture an image from the detection zone. In an exemplary embodiment, the processing unit may be electrically connected to the image-capturing device. In an exemplary embodiment, the processing unit may include a memory having processor-readable instructions stored therein and a processor. In an exemplary embodiment, the processor may be configured to access the memory and execute the processor-readable instructions. In an exemplary embodiment, the processor may be configured to perform a method by executing the processor-readable instructions. In an exemplary embodiment, the method may include capturing a first image from the detection zone before injection of the saliva sample utilizing the image-capturing device, capturing a second image from the detection zone after at least four minutes of interaction between the injected saliva sample and the array of chemical receptors utilizing the image-capturing device, and detecting a COVID-19 infection status of the person by analyzing color changes of the array of chemical receptors in the second image respective to the first image.

In an exemplary embodiment, the array of chemical receptors may include a first array of chemical receptors including at least one plurality of functionalized nanoparticles, a second array of chemical receptors including at least one pH-sensitive organic dye, a third array of chemical receptors including at least one Lewis donor or at least one Lewis acceptor, and a fourth array of chemical receptors including at least one metal ion complex. In an exemplary embodiment, the at least one plurality of functionalized nanoparticles may include at least one plurality of gold nanoparticles (AuNPs) functionalized with at least one of bovine serum albumin (BSA), caffeic acid (CA), poly glutamic acid (PGA), and combinations thereof. In an exemplary embodiment, each chemical receptor of the first array of chemical receptors may include an aqueous solution of the at least one plurality of functionalized nanoparticles with a concentration of 4.5 mg mL$^{-1}$. In an exemplary embodiment, each chemical receptor of the second array of chemical receptors may include a mixture of an organic dye with an additive. In an exemplary embodiment, the organic dye may include at least one of bromophenol red, bromocresol purple, and combinations thereof. In an exemplary embodiment, the additive may include at least one of DWES, phenylboronic acid (PBA), and combinations thereof, where DWES is a mixture of 2, 4-dinitrophenylhydrazine, deionized water, Ethanol (EtOH), and $H_2SO_4$. In an exemplary embodiment, each chemical receptor of the second array of chemical receptors may include a solution of the mixture of the organic dye with the additive in ethanol (EtOH) with a volume ratio of organic dye:additive equal to 3:1. In an exemplary embodiment, the at least one Lewis donor or the at least one Lewis acceptor may include at least one porphyrin-based dye. In an exemplary embodiment, the at least one porphyrin-based dye may include at least one of [meso-tetraphenylporphyrin]Iron(III) chloride (Fe(III)TPPCl), [meso-tetraphenylporphyrin]-Tin (II) (Sn(II)TPP), meso-tetrakis(4-hydroxyphenyl) porphyrin-manganese (III) acetate (Mn(III)T(4-OH)PP(OAc)), and combinations thereof. In an exemplary embodiment, each chemical receptor of the third array of chemical receptors may include a solution of the at least one Lewis donor or the at least one Lewis acceptor with a concentration of 4.5 mg mL$^{-1}$ in Ethanol. In an exemplary embodiment, the at least one metal ion complex may include a complex of at least one organic dye and at least one metal ion. In an exemplary embodiment, the at least one metal ion complex may include a complex of pyrocatechol violet (Py) with at least one of V (IV) ions, Fe (III) ions, Fe (II) ions, Cu (II) ions, Ni (II) ions, and combinations thereof. In an exemplary embodiment, each chemical receptor of the fourth array of chemical receptors may include a solution of the at least one metal ion complex with a concentration of 0.05 mol L$^{-1}$ in a buffer solution with pH value of 9.0.

In an exemplary embodiment, the system may further include two planar holders configured to retain the injection zone and the detection zone firmly folded on each other between the two planar holders. In an exemplary embodiment, the two planar holders may include a first planar holder and a second planar holder. In an exemplary embodiment, the first planar holder may include a first sheet made of poly(methyl methacrylate) (PMMA) and the second planar holder may include a second sheet made of PMMA. In an exemplary embodiment, the first planar holder may be configured to be fixed on a surface of the injection zone. In an exemplary embodiment, the first planar holder may include a hole configured to inject the saliva sample there through on the injection zone. In an exemplary embodiment, the second planar holder may be configured to be fixed on a surface of the detection zone.

In an exemplary embodiment, analyzing color changes of the array of chemical receptors in the second image respective to the first image may include generating a first color value vector associated with the first image, generating a second color value vector associated with the second image, generating a difference color value vector associated with the saliva sample by subtracting each color value of the first color value vector from a respective color value of the second color value vector, and detecting the COVID-19 infection status of the person based on the difference color value vector. In an exemplary embodiment, the first color value vector may include a first array of a respective first set of three numerical color values of three respective color components of color of each respective chemical receptor of the array of chemical receptors in the first image. In an exemplary embodiment, the three color components may include red, green, and blue. In an exemplary embodiment, the second color value vector may include a second array of a respective second set of three numerical color values respective to the three color components of color of each respective chemical receptor of the array of chemical receptors in the second image.

In an exemplary embodiment, each of the first color value vector and the second color value vector is defined by a relation as follows:

$$V_j=[R_{1j}G_{1j}B_{1j} \ldots R_{ij}G_{ij}B_{ij} \ldots R_{nj}G_{nj}B_{nj}],$$

Where, j is equal to 1 for the first image and is equal to 2 for the second image, $R_{ij}$ is red component value of color of $i^{th}$ chemical receptor of the array of chemical receptors in the $j^{th}$ image, $G_{ij}$ is green component value of color of $i^{th}$ chemical receptor of the array of chemical receptors in the $j^{th}$ image, $B_{ij}$ is blue component value of color of $i^{th}$ chemical receptor of the array of chemical receptors in the $j^{th}$ image, and n comprises total number of chemical receptors of the array of chemical receptors.

In an exemplary embodiment, the difference color value vector may be defined by a relation as follows:

$$\Delta V=[\Delta R_1 \Delta G_1 \Delta B_1 \ldots \Delta R_i \Delta G_i \Delta B_i \ldots \Delta R_n \Delta G_n \Delta B_n],$$

Where, $\Delta R_i$ is defined by a relation of $\Delta R_i=R_{i2}-R_{i1}$, $\Delta G_i$ is defined by a relation of $\Delta G_i=G_{i2}-G_{i1}$, and $\Delta B_i$ is defined by a relation of $\Delta B_i=B_{i2}-B_{i1}$.

In an exemplary embodiment, detecting the COVID-19 infection status of the person based on the difference color value vector may include calculating a magnitude of the difference color value vector and detecting the COVID-19 infection status of the person. In an exemplary embodiment, calculating the magnitude of the difference color value vector may be done using a relation defined as follows:

$$|\Delta V|=\sqrt{\Sigma_{i=1}^{n}(\Delta R_i)^2+(\Delta G_i)^2+(\Delta B_i)^2},$$

Where, $|\Delta V|$ is the magnitude of the difference color value vector. In an exemplary embodiment, detecting the COVID-19 infection status of the person may include detecting the person is healthy if the magnitude of the difference color value vector is more than a threshold value or detecting the person is COVID-19 infected if the magnitude of the difference color value vector is less than the threshold value. In an exemplary embodiment, the threshold value may include a value of 342.4. In an exemplary embodiment, the array of chemical receptors may include an array of functionalized nanoparticles, an array of pH-sensitive organic dyes, an array of three solutions of three respective porphyrin-based dyes with a concentration of 4.5 mg mL$^{-1}$ in ethanol, and an array of three solutions of three respective metal ion complexes with a concentration of 0.05 mol L$^{-1}$ in a borate buffer solution with pH value of 9.0.

In an exemplary embodiment, the array of functionalized nanoparticles may include three aqueous solutions of three respective functionalized AuNPs with a concentration of 4.5 mg mL$^{-1}$. In an exemplary embodiment, the three functionalized AuNPs may include AuNPs functionalized with BSA (BSA-AuNPs), AuNPs functionalized with CA (CA-AuNPs), and AuNPs functionalized with PGA (PGA-AuNPs). In an exemplary embodiment, the array of pH-sensitive organic dyes may include three solutions of three respective mixtures of an organic dye and an additive with a volume ratio of organic dye:additive equal to 3:1 in ethanol. In an exemplary embodiment, the three mixtures of the organic dye and the additive may include a mixture of bromophenol red and DWES, a mixture of bromocresol purple and DWES, and a mixture of bromophenol red and PBA. In an exemplary embodiment, the three porphyrin-based dyes may include Fe(III)TPPCl, Mn(III)T(4-OH)PP (OAc), and Sn(II)TPP. In an exemplary embodiment, the three metal ion complexes may include a complex of Py with V (IV) ions, a complex of Py with Fe (II) ions, and a complex of Py with Cu (II) ions.

In an exemplary embodiment, detecting the COVID-19 infection status of the person based on the difference color value vector may include comparing each element of the difference color value vector with a respective element of a set of reference difference color value vectors and detecting the person being one of a COVID-19 infected patient, a healthy individual, or a cured individual after an infection with COVID-19 virus. In an exemplary embodiment, an exemplary set of reference difference color value vectors may include a first reference difference color value vector including a mean difference color value vector of a first plurality of difference color value vectors associated with a respective first plurality of saliva samples acquired from a respective plurality of COVID-19 patients, a second reference difference color value vector including a mean difference color value vector of a second plurality of difference color value vectors associated with a respective second plurality of saliva samples acquired from a respective plurality of healthy individuals, and a third reference difference color value vector including a mean difference color value vector of a third plurality of difference color value vectors associated with a respective third plurality of saliva samples acquired from a respective plurality of cured individuals after a COVID-19 infection. In an exemplary embodiment, detecting the person being one of a COVID-19 infected patient, a healthy individual, or a cured individual after an infection with COVID-19 virus may include one of detecting the person is a COVID-19 infected patient if a difference percentage between each element of the difference color value vector and the respective element of the first reference difference color value vector is less than 5%, detecting the person is a healthy individual if a difference percentage between each element of the difference color value vector and the respective element of the second reference difference color value vector is less than 5%, or detecting the person is a cured individual after a COVID-19 infection if a difference percentage between each element of the difference color value vector and the respective element of the third reference difference color value vector is less than 5%. In an exemplary embodiment, the method may further include generating the set of reference difference color value vectors. In an exemplary embodiment, generating the set of reference difference color value vectors may include generating a set of three pluralities of difference color value vectors and forming the set of reference difference color value vectors by calculating a respective average vector of each plurality of difference color value vectors of the three pluralities of difference color value vectors. In an exemplary embodiment, generating the set of three pluralities of difference color value vectors may include generating the first plurality of difference color value vectors associated with the respective first plurality of saliva samples acquired from the respective plurality of COVID-19 patients, generating the second plurality of difference color value vectors associated with the respective second plurality of saliva samples acquired from the respective plurality of healthy individuals, and generating the third plurality of difference color value vectors associated with the respective third plurality of saliva samples acquired from the respective plurality of cured individuals after a COVID-19 infection. In an exemplary embodiment, forming the set of reference difference color value vectors may include calculating an average of each respective element in the first plurality of difference color value vectors, calculating an average of each respective element in the second plurality of difference color value vectors, and calculating an average of each respective element in the third plurality of difference color value vectors.

In an exemplary embodiment, detecting COVID-19 infection status of an exemplary saliva sample may further include detecting a severity grade of COVID-19 infection of an exemplary person. In an exemplary embodiment, detecting a severity grade of COVID-19 infection of an exemplary person may include extracting two sets of three numerical color values of the second pH-sensitive organic dye in the first image and the second image, generating a difference color value vector associated with the second pH-sensitive organic dye by subtracting the two sets of three numerical color values from each other, calculating a magnitude of discoloration of the second pH-sensitive organic dye in the second image respective to the first image, and detecting severity grade of COVID-19 infection of an exemplary person based on the calculated magnitude of discoloration of the second pH-sensitive organic dye in the second image respective to the first image. In an exemplary embodiment, the three numerical color values may include respective values of three color components of color of the second pH-sensitive organic dye. In an exemplary embodiment, the three color components may include red, green, and blue.

In an exemplary embodiment, calculating the magnitude of discoloration of the second pH-sensitive organic dye in the second image respective to the first image may include calculating magnitude of the difference color value vector associated with the second pH-sensitive organic dye. In an exemplary embodiment, the magnitude of the difference color value vector associated with the second pH-sensitive organic dye may be calculated using a relation defined by:

$$|\Delta V| = \sqrt{(\Delta R)^2 + (\Delta G)^2 + (\Delta B)^2},$$

Where, $|\Delta V|$ is the magnitude of discoloration of the second pH-sensitive organic dye, $\Delta R$ is a difference between respective red color values in the first image and the second image, $\Delta G$ is a difference between respective green color values in the first image and the second image, and $\Delta B$ is a difference between respective blue color values in the first image and the second image.

In an exemplary embodiment, detecting the severity grade of COVID-19 infection of an exemplary person based on the calculated magnitude of discoloration of the second pH-sensitive organic dye in the second image respective to the first image may include one of detecting an exemplary person is mildly infected by COVID-19 virus, detecting an exemplary person is moderately infected by COVID-19 virus, detecting an exemplary person is severely infected by COVID-19 virus, and detecting an exemplary person is highly-severe infected by COVID-19 virus. In an exemplary embodiment, detecting the severity grade of COVID-19 infection of an exemplary person may include detecting the person is mildly infected by COVID-19 virus if the magnitude of discoloration of the second pH-sensitive organic dye is in a range of 0 to 150. In an exemplary embodiment, a mildly infection by COVID-19 virus may include a cycle threshold (CT) number in a range of 28 to 32. In an exemplary embodiment, an exemplary CT number may include a CT number for N gene obtained in a polymerase-chain-reaction (PCR) test applied to an exemplary person. In an exemplary embodiment, detecting the severity grade of COVID-19 infection of an exemplary person may include detecting the person is moderately infected by COVID-19 virus if the magnitude of discoloration of the second pH-sensitive organic dye is in a range of 150 to 160. In an exemplary embodiment, a moderately infection by COVID-19 virus may include a CT number in a range of 23 to 27. In an exemplary embodiment, detecting the severity grade of COVID-19 infection of an exemplary person may include detecting the person is severely infected by COVID-19 virus if the magnitude of discoloration of the second pH-sensitive organic dye is in a range of 160 to 180. In an exemplary embodiment, a severely infection by COVID-19 virus may include a CT number in a range of 18 to 22. In an exemplary embodiment, detecting the severity grade of COVID-19 infection of an exemplary person may include detecting the person is highly-severe infected by COVID-19 virus if the magnitude of discoloration of the second pH-sensitive organic dye is in a range of 180 to 220. In an exemplary embodiment, a highly-severe infection by COVID-19 virus may include a CT number in a range of 15 to 17.

BRIEF DESCRIPTION OF THE DRAWINGS

The drawing figures depict one or more embodiments in accord with the present teachings, by way of example only, not by way of limitation. In the figures, like reference numerals refer to the same or similar elements.

DETAILED DESCRIPTION

Figure 1A:
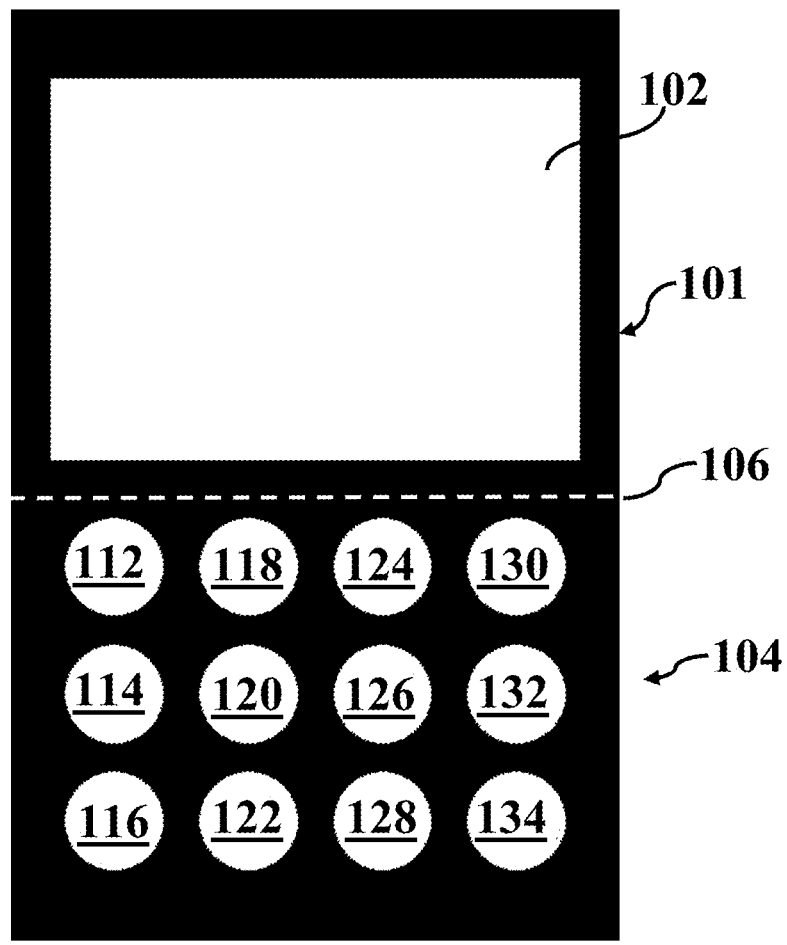
FIG. 1A illustrates a schematic view of an exemplary colorimetric sensor for detecting a disease by analyzing an exemplary saliva sample, consistent with one or more exemplary embodiments of the present disclosure.

In the following detailed description, numerous specific details are set forth by way of examples in order to provide a thorough understanding of the relevant teachings. However, it should be apparent that the present teachings may be practiced without such details. In other instances, well known methods, procedures, components, and/or circuitry have been described at a relatively high-level, without detail, in order to avoid unnecessarily obscuring aspects of the present teachings. The following detailed description is presented to enable a person skilled in the art to make and use the methods and devices disclosed in exemplary embodiments of the present disclosure. For purposes of explanation, specific nomenclature is set forth to provide a thorough understanding of the present disclosure. However, it will be apparent to one skilled in the art that these specific details are not required to practice the disclosed exemplary embodiments. Descriptions of specific exemplary embodiments are provided only as representative examples. Various modifications to the exemplary embodiments will be readily apparent to one skilled in the art, and the general principles defined herein may be applied to other embodiments and applications without departing from the scope of the present disclosure. The present disclosure is not intended to be limited to the embodiments shown, but is to be accorded the widest possible scope consistent with the principles and features disclosed herein.

The present disclosure is directed to exemplary systems and methods to detect a disease or respiratory and body disorders of a person using a saliva sample acquired from the person. In an exemplary embodiment, an infection with COVID-19 virus may be detected using an exemplary saliva sample utilizing exemplary method and/or system disclosed herein. In an exemplary embodiment, smokers and people with kidney disease and diabetes may be identified using an exemplary saliva sample utilizing exemplary method and/or system disclosed herein. In an exemplary embodiment, a severity of COVID-19 infection may be further detected utilizing exemplary method and/or system. In an exemplary embodiment, a COVID-19 status of a person may be detected one of an infection with COVID-19 virus, a healthy status, or a cured status after a COVID-19 infection utilizing exemplary method and/or system disclosed herein. In an exemplary embodiment, exemplary system may include a colorimetric sensor, an image-capturing device, and a processing unit electrically connected to exemplary image-capturing device. In an exemplary embodiment, exemplary colorimetric sensor may include a hydrophilic paper with two separately zones, including an injection zone and a detection zone. In an exemplary embodiment, exemplary detection zone may include an array of chemical receptors coated on a respective array of individual zones patterned on exemplary detection zone. In an exemplary embodiment, exemplary injection zone and detection zone may be separated from each other using a hydrophobic barrier coated on parts between exemplary injection zone and detection zone. Furthermore, zones of exemplary array of individual zones may be isolated from each other using exemplary hydrophobic barrier coated on parts of detection zone among zones of exemplary array of individual zones. In an exemplary embodiment, exemplary hydrophobic barrier may be configured to prevent flow or penetration of a fluid (e.g., a saliva sample) from one zone of exemplary array of individual zones to another. In an exemplary embodiment, exemplary hydrophilic paper may be folded and exemplary injection zone may be placed on exemplary detection zone so that exemplary injection zone may cover whole array of individual zones of exemplary detection zone. In an exemplary embodiment, a saliva sample may be injected on exemplary injection zone and an injected saliva sample may penetrate vertically from injection zone to detection zone. In an exemplary embodiment, exemplary array of chemical receptors may include a plurality of chemical receptors being interactive with metabolites of an exemplary saliva sample. In an exemplary embodiment, array of chemical receptors may discolor with a discriminative manner responsive to an interaction with specific metabolites of exemplary saliva sample associated with a disease. In an exemplary embodiment, a first group of chemical receptors may discolor responsive to an interaction with a first group of metabolites, which are chemical markers of COVID-19 infection and are present in an exemplary saliva sample of a COVID-19 patient. In an exemplary embodiment, a second group of chemical receptors may discolor responsive to an interaction with a second group of metabolites, which are chemical markers of normal status and are present in an exemplary saliva sample of a healthy individual. In an exemplary embodiment, a third group of chemical receptors may discolor responsive to an interaction with a third group of metabolites, which are chemical markers of cured COVID-19 infection and are present in an exemplary saliva sample of a cured individual after a COVID-19 infection. As used herein, a "cured individual" may refer to a cured COVID-19-infected patient. In an exemplary embodiment, a "cured individual" may refer to a COVID-19-infected patient who had been treated and at least two months passed from his/her recovery. In an exemplary embodiment, an image may be captured from exemplary detection zone after a pre-determined period of time of interaction between an exemplary saliva sample and an array of chemical receptors. In an exemplary embodiment, an exemplary pre-determined period of time may include at least four minutes. In an exemplary embodiment, a COVID-19 infection status may be detected by comparing discoloration of an exemplary array of chemical receptors in an exemplary captured image after interaction respective to an initial image captured from an exemplary array of chemical receptors before injection a saliva sample on exemplary injection zone. In an exemplary embodiment, discoloration of an exemplary array of chemical receptors may be compared with discolorations recorded in a plurality of captured images from an exemplary array of chemical receptors after interaction with a respective plurality of saliva samples acquired from a respective plurality of individuals with known status of COVID-19 infection. In an exemplary embodiment, an exemplary saliva sample may be detected to be associated with a COVID-19 infected patient if discoloration of an exemplary array of chemical receptors after interaction with exemplary saliva sample is in a range of discolorations of exemplary array of chemical receptors after interaction with a first set of saliva samples acquired from known COVID-19 patients. In an exemplary embodiment, an exemplary saliva sample may be detected to be associated with a healthy individual if discoloration of an exemplary array of chemical receptors after interaction with exemplary saliva sample is in a range of discolorations of exemplary array of chemical receptors after interaction with a second set of saliva samples acquired from known healthy people. In an exemplary embodiment, an exemplary saliva sample may be detected to be associated with a cured individual if discoloration of an exemplary array of chemical receptors after interaction with exemplary saliva sample is in a range of discolorations of exemplary array of chemical receptors after interaction with a third set of saliva samples acquired from known cured individuals.

Figure 1B:
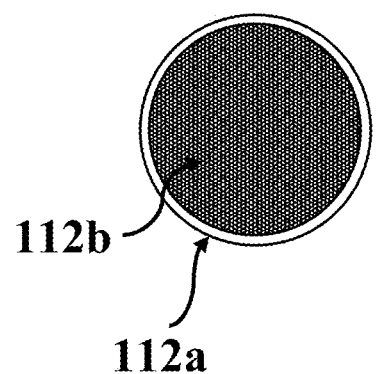
FIG. 1B illustrates a schematic view of an exemplary sensing zone of an exemplary array of sensing zones, consistent with one or more exemplary embodiments of the present disclosure.
Figure 1C:
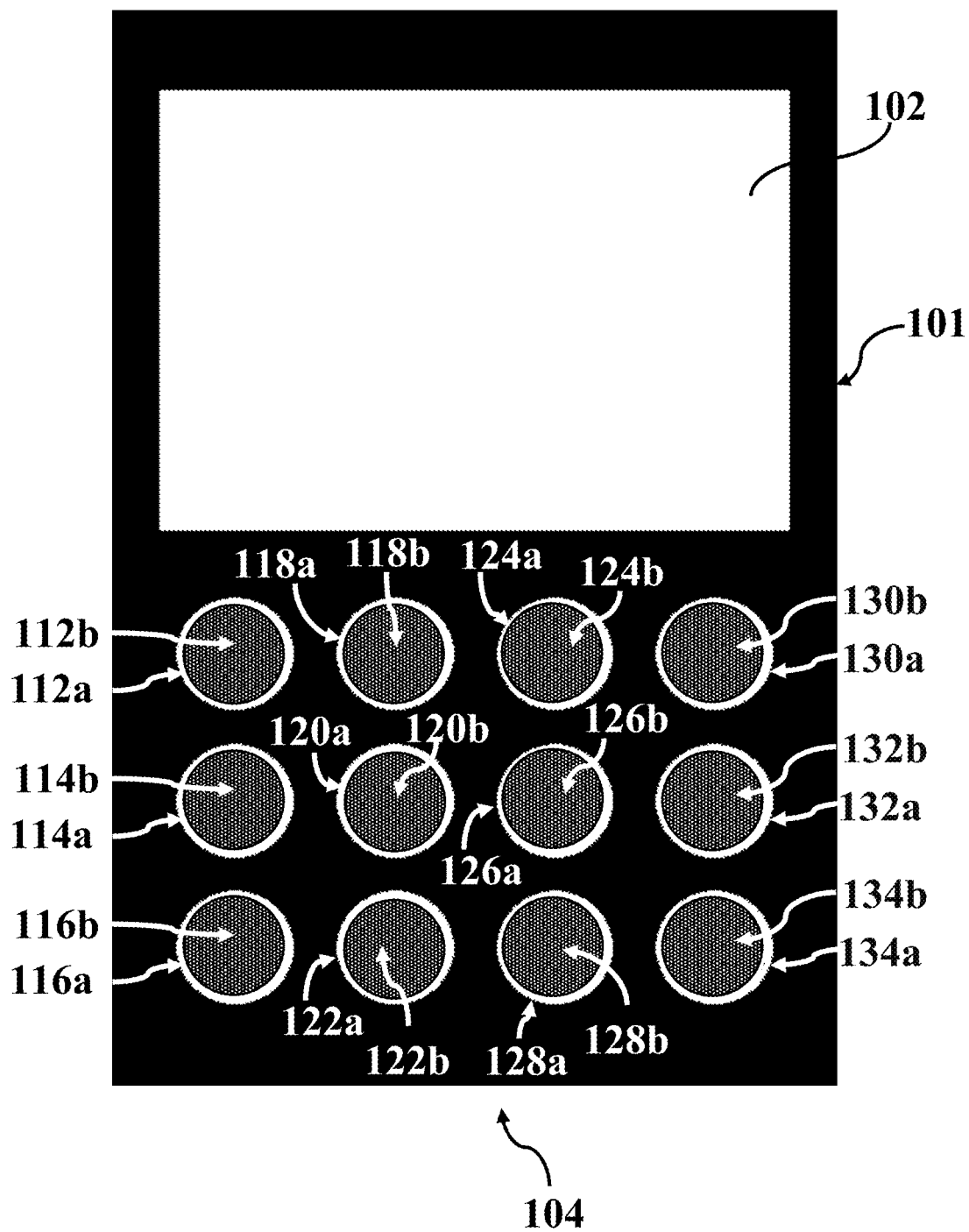
FIG. 1C illustrates another schematic view of an exemplary colorimetric sensor for detecting a disease by analyzing an exemplary saliva sample, consistent with one or more exemplary embodiments of the present disclosure.

FIG. 1A illustrates a schematic view of a colorimetric sensor 100 for detecting a disease by analyzing an exemplary saliva sample, consistent with one or more exemplary embodiments of the present disclosure. In an exemplary embodiment, colorimetric sensor 100 may be utilized by system 200 and/or one or more steps of method 300 illustrated herein below. In an exemplary embodiment, colorimetric sensor 100 may be used to detect COVID-19 infection of a person using a saliva sample acquired from the person. In an exemplary embodiment, colorimetric sensor 100 may include an exemplary injection zone 102, an exemplary detection zone 104, and an exemplary hydrophobic barrier 101. In an exemplary embodiment, injection zone 102 may include a bare part of a hydrophilic paper. In an exemplary embodiment, the hydrophilic paper may include a cellulosic paper. In an exemplary embodiment, detection zone 104 may include an array of sensing zones 112 to 134. FIG. 1B illustrates a schematic view of an exemplary sensing zone 112 of an exemplary array of sensing zones 112 to 134, consistent with one or more exemplary embodiments of the present disclosure. Referring to FIG. 1B, an exemplary sensing zone 112 of array of sensing zones 112 to 134 may include a chemical receptor 112b deposited (or coated) on a respective individual area 112a. In an exemplary embodiment, each respective sensing zone (similar to exemplary sensing zone 112) of array of sensing zones 112 to 134 may include a respective chemical receptor (similar to chemical receptor 112b) deposited (or coated) on a respective individual area (similar to individual area 112a). FIG. 1C illustrates another schematic view of exemplary colorimetric sensor 100 for detecting a disease by analyzing an exemplary saliva sample, consistent with one or more exemplary embodiments of the present disclosure. In an exemplary embodiment, exemplary array of sensing zones 112 to 134 may include a respective array of individual areas 112a to 134a patterned on detection zone 104. In an exemplary embodiment, each respective individual area of exemplary array of individual areas 112a to 134a may be an array of bare individual areas of an exemplary hydrophilic paper separated (isolated) from each other by hydrophobic barrier 101. In an exemplary embodiment, each respective individual area of exemplary array of individual areas 112a to 134a may have a circular shape. In an exemplary embodiment, exemplary array of sensing zones 112 to 134 may further include a respective array of chemical receptors 112b to 134b coated on respective array of individual areas 112a to 134a. In an exemplary embodiment, an exemplary chemical receptor may include a chemical receptor of a respective chemical marker of COVID-19 infection in an exemplary saliva sample. In an exemplary embodiment, detection zone 104 may include exemplary array of individual areas 112a to 134a coated with respective array of chemical receptors 112b to 134b. In an exemplary embodiment, injection zone 102 and exemplary array of sensing zones 112 to 134 may be separated (isolated) from each other by hydrophobic barrier 101. In an exemplary embodiment, hydrophobic barrier 101 may include a hydrophobic material filled in texture of an exemplary hydrophilic paper around injection zone 102 and detection zone 104, and within spaces among exemplar array of sensing zones 112 to 134. In an exemplary embodiment, hydrophobic barrier 101 may include a hydrophobic material filled in parts of texture of an exemplary hydrophilic paper except injection zone 102 and array of sensing zones 112 to 134. In an exemplary embodiment, hydrophobic barrier 101 may include a hydrophobic ink printed on parts of an exemplary hydrophilic paper except injection zone 102 and detection zone 104. In an exemplary embodiment, an exemplary printed hydrophobic ink on parts of an exemplary hydrophilic paper except injection zone 102 and detection zone 104 may be penetrated into respective parts of texture of an exemplary hydrophilic paper except injection zone 102 and detection zone 104 by heating an exemplary hydrophilic paper. In an exemplary embodiment, hydrophobic barrier 101 may isolate injection zone 102 from detection zone 104. In an exemplary embodiment, hydrophobic barrier 101 may further isolate sensing zones 112 to 134 from each other. In an exemplary embodiment, hydrophobic barrier 101 may be configured to prevent penetration or spillover of a fluid, for example, an exemplary saliva sample from a first sensing zone of exemplary array of sensing zones 112 to 134 to a second sensing zone of exemplary array of sensing zones 112 to 134. In an exemplary embodiment, detection zone 104 may include an array of 12 sensing zones 112 to 134 (illustrated in FIG. 1A) coated with an exemplary respective array of 12 chemical receptors. In an exemplary embodiment, injection zone 102 and an exemplary array of sensing zones 112 to 134, illustrated in white color in FIG. 1A, may be separated (isolated) from each other by hydrophobic barrier 101 illustrated in black color in FIG. 1A. In an exemplary embodiment, hydrophobic barrier 101 may include a hydrophobic material filled in texture of an exemplary hydrophilic paper around injection zone 102 and detection zone 104, and within spaces among sensing zones 112 to 134. In an exemplary embodiment, hydrophobic barrier 101 may be configured to prevent penetration of a fluid (e.g., an exemplary saliva sample) from a first sensing zone of array of 12 sensing zones 112 to 134 to a second sensing zone of array of 12 sensing zones 112 to 134.

In an exemplary embodiment, an exemplary chemical receptor of exemplary array of chemical receptors 112b to 134b of detection zone 104 may include a chemical compound with a color reagent. In an exemplary embodiment, color of an exemplary chemical receptor of exemplary array of chemical receptors 112b to 134b of detection zone 104 may change due to an interaction between an exemplary chemical receptor and an analyte. In an exemplary embodiment, an exemplary analyte may include a chemical marker of a disease in a sample acquired from a person suspected to have the disease. In an exemplary embodiment, an exemplary chemical receptor of exemplary array of chemical receptors 112b to 134b of detection zone 104 may include a chemical agent capable of recoloring by interacting with a chemical marker of COVID-19 in an exemplary saliva sample. In an exemplary embodiment, an exemplary chemical marker of COVID-19 may include a chemical compound in saliva having different amounts in a saliva sample acquired from a COVID-19 infected patient and a saliva sample acquired from a healthy individual. In an exemplary embodiment, color of an exemplary chemical agent may change due to chemically interacting with an exemplary chemical in saliva with an amount of more than a threshold. In an exemplary embodiment, chemicals such as $C_{25}H_{36}N_6O_6$, DL-phenylalanine, $C_7H_{10}N_6O_2$, 2-linoleoyl-sn-glycero-3-phosphoethanolamine, $C_{39}H_{71}N_2O_{16}P_3$, 1-hexadecanoylpyrrolidine, taurine, $C_{47}H_{84}N_9O_{13}P_3$, and $C_{22}H_{36}N_8O_9$ may have different amounts in saliva samples of healthy individuals and COVID-19 patients. In an exemplary embodiment, an exemplary chemical agent may have active sites capable of reacting with functional groups of chemical compounds in an exemplary saliva sample via one or more chemical interactions, including Lewis acid-base reactions, Brunsted acid base reactions, hydrogen bonding, covalent bonding, indicator displacement, and/or electrostatic interactions. These chemical interactions may cause formation of at least one of a new chemical, accumulation of particles, a change in nature of structure of an exemplary chemical agent; thereby, leading to alter optical properties of an exemplary chemical agent and change color of an exemplary chemical agent. In an exemplary embodiment, chemical receptors of four main groups may be used to be coated individually on exemplary array of array of individual areas 112a to 134a of detection zone 104. In an exemplary embodiment, dye-based proton donors and acceptors (e.g., pH-sensitive organic dyes), material-based electron donors and acceptors (i.e., Lewis donors and/or Lewis acceptors), metal ion complexes, and nanoparticles may be used as chemical receptors coated on exemplary array of array of individual areas 112a to 134a of detection zone 104; thereby, interacting with target COVID-19 chemical markers in an exemplary saliva sample. In an exemplary embodiment, utilizing a range of different main groups of chemical receptors and additionally, using different chemical receptors in each main group with different reactivities with chemical markers of COVID-19 infection may result in enhancing detection ability of colorimetric sensor 100 in the presence of ultra-low amounts of chemical markers associated with COVID-19 infection in an exemplary saliva sample and increasing an efficiency of colorimetric sensor 100 to differentiating between saliva samples acquired from infected patients and healthy individuals.

In an exemplary embodiment, an exemplary array of chemical receptors, such as array of chemical receptors 112b to 134b, may include a first array of chemical receptors, such as array of chemical receptors 112b, 114b, and 116b, including at least one plurality of functionalized nanoparticles, a second array of chemical receptors, such as array of chemical receptors 118b, 120b, and 122b, including at least one pH-sensitive organic dye, a third array of chemical receptors, such as array of chemical receptors 124b, 126b, and 128b, including at least one Lewis donor or at least one Lewis acceptor, and a fourth array of chemical receptors, such as array of chemical receptors 130b, 132b, and 134b, including at least one metal ion complex. In an exemplary embodiment, the at least one plurality of functionalized nanoparticles may include at least one plurality of gold nanoparticles (AuNPs) functionalized with at least one of bovine serum albumin (BSA), caffeic acid (CA), poly glutamic acid (PGA), and combinations thereof. In an exemplary embodiment, each chemical receptor of the first array of chemical receptors may include an aqueous solution of the at least one plurality of functionalized nanoparticles with a concentration in a range of 1.5 mg mL$^{-1}$ to 6.0 mg mL$^{-1}$. In an exemplary embodiment, each chemical receptor of the first array of chemical receptors may include an aqueous solution of the at least one plurality of functionalized nanoparticles with a concentration of 4.5 mg mL$^{-1}$. In an exemplary embodiment, each chemical receptor of the second array of chemical receptors may include a mixture of an organic dye with an additive. In an exemplary embodiment, the organic dye may include at least one of bromophenol red, bromocresol purple, and combinations thereof. In an exemplary embodiment, the additive may include at least one of DWES, phenylboronic acid (PBA), and combinations thereof. As used herein, "DWES" is a mixture of 2, 4-dinitrophenylhydrazine, deionized water, Ethanol (EtOH), and $H_2SO_4$. In an exemplary embodiment, DWES is a mixture of 0.4 gr of 2, 4-dinitrophenylhydrazine, 3.0 mL of deionized water, 10.0 mL of Ethanol (EtOH), and 2.0 mL of $H_2SO_4$. In an exemplary embodiment, each chemical receptor of the second array of chemical receptors may include a solution of the mixture of the organic dye with the additive in ethanol (EtOH) with a volume ratio of organic dye:additive in a range of 3:1 to 5:1. In an exemplary embodiment, each chemical receptor of the second array of chemical receptors may include a solution of the mixture of the organic dye with the additive in ethanol (EtOH) with a volume ratio of organic dye:additive equal to 3:1. In an exemplary embodiment, the at least one Lewis donor or the at least one Lewis acceptor may include at least one porphyrin-based dye. In an exemplary embodiment, the at least one porphyrin-based dye may include at least one of [meso-tetraphenylporphyrin] Iron(III) chloride (Fe(III)TPPCl), [meso-tetraphenylporphyrin]-Tin (II) (Sn(II)TPP), meso-tetrakis(4-hydroxyphenyl) porphyrin-manganese (III) acetate (Mn(III)T(4-OH)PP (OAc)), and combinations thereof. In an exemplary embodiment, each chemical receptor of the third array of chemical receptors may include a solution of the at least one Lewis donor or the at least one Lewis acceptor with a concentration in a range of 1.5 mg mL$^{-1}$ to 6.0 mg mL$^{-1}$. In an exemplary embodiment, each chemical receptor of the third array of chemical receptors may include a solution of the at least one Lewis donor or the at least one Lewis acceptor with a concentration of 4.5 mg mL$^{-1}$ in Ethanol. In an exemplary embodiment, the at least one metal ion complex may include a complex of at least one organic dye and at least one metal ion. In an exemplary embodiment, the at least one metal ion complex may include a complex of pyrocatechol violet (Py) with at least one of V (IV) ions, Fe (III) ions, Fe (II) ions, Cu (II) ions, Ni (II) ions, and combinations thereof. In an exemplary embodiment, each chemical receptor of the fourth array of chemical receptors may include a solution of the at least one metal ion complex with a concentration of metal ion complex in a range of 0.005 mol L$^{-1}$ to 0.1 mol L$^{-1}$ in a buffer solution with pH value in a range 3.0 to 11.0. In an exemplary embodiment, each chemical receptor of the fourth array of chemical receptors may include a solution of the at least one metal ion complex with a concentration of 0.05 mol L$^{-1}$ in a buffer solution with pH value of 9.0.

In an exemplary embodiment, each three sensing zones of array of 12 sensing zones 112 to 134 may include three different chemical receptors 112b, 114b, and 116b of one main group of exemplary four main groups of chemical receptors coated on respective individual areas 112a, 114a, and 116a. In an exemplary embodiment, sensing zones 112, 114, and 116 may include three respective chemical receptors of nanoparticle-based chemical receptors. In an exemplary embodiment, sensing zones 112, 114, and 116 may include three respective pluralities of functionalized nanoparticles. In an exemplary embodiment, sensing zones 112, 114, and 116 may include three respective gold nanoparticles (AuNPs)-containing chemical receptors. In an exemplary embodiment, each sensing zone of sensing zones 112, 114, and 116 may include a respective aqueous solution of a gold nanoparticles (AuNPs)-containing chemical receptor coated on the respective sensing zone. In an exemplary embodiment, an exemplary aqueous solution of an exemplary AuNPs-containing chemical receptor may include an exemplary AuNPs-containing chemical receptor particles dispersed in deionized water with a concentration in a range of 1.5 mg L$^{-1}$ to 6.0 mg L$^{-1}$. In an exemplary embodiment, an exemplary aqueous solution of an exemplary AuNPs-containing chemical receptor may include an exemplary AuNPs-containing chemical receptor particles dispersed in deionized water with a concentration of 4.5 mg L$^{-1}$. In an exemplary embodiment, each sensing zone of sensing zones 112, 114, and 116 may include a respective plurality of functionalized AuNPs. In an exemplary embodiment, functionalized AuNPs may include AuNPs coated by a capping agent. In an exemplary embodiment, an exemplary capping agent may include at least one of Bovine serum albumin (BSA), caffeic acid (CA), and poly glutamic acid (PGA). In an exemplary embodiment, sensing zone 112 may include BSA-AuNPs coated on individual area 112a. In an exemplary embodiment, sensing zone 114 may include CA- AuNPs coated on individual area 114*a*. In an exemplary embodiment, sensing zone 116 may include PGA-AuNPs coated on individual area 116*a*. In an exemplary embodiment, specific properties of AuNPs, such as surface plasmon resonance, high surface-to-volume ratio and molecular recognition properties may provide AuNPs being effective detecting elements for marker ions and chemical compounds of a disease, for example, COVID-19 infection so that color of sensing zones 112, 114, and 116 may change responsive to an interaction with an exemplary saliva sample of a COVID-19 infected patient.

In an exemplary embodiment, functional groups of exemplary of capping agents, size of functionalized AuNPs, and electrical charge on surface of functionalized AuNPs may increase selectivity of functionalized AuNPs for detecting COVID-19 markers in an exemplary saliva sample. Herein, using AuNPs functionalized with three different functional groups BSA, CA, and PGA in three respective sensing zones 112, 114, and 116 may lead to high distinct, selective, and accurate discoloration of AuNPs in response to saliva markers of distinct groups of healthy, cured, and COVID-19 infected individuals. In an exemplary embodiment, functional groups of exemplary of capping agents may include at least one of amino groups, carboxylic groups, ketone groups, aldehyde groups, hydroxyl groups, and combinations thereof In an exemplary embodiment, functional groups of exemplary of capping agents may interact with active sites of metabolites of saliva via H-bonding, nucleophilic, or electrophilic interactions. In an exemplary embodiment, surface of each nanoparticle may be coated with a positive or negative electric charge that may electrostatically interact with species with opposite charges in an exemplary saliva sample. In an exemplary embodiment, size of capping agents on nanoparticles surface may be in a wide range. However, functionalized AuNPs with smaller capping agents may easily react with all metabolites in an exemplary saliva sample, but functionalized AuNPs with larger capping agents may not react with structurally bulky metabolites of an exemplary saliva sample due to limited interactions resulted by space disturbance of larger capping agents.

Furthermore, sensing zones 118, 120, and 122 may include three different dye-based proton donors and/or acceptors 118*b*, 120*b*, and 122*b* coated on respective three individual areas 118*a*, 120*a*, and 122*a*. In an exemplary embodiment, a dye-based proton donor or acceptor may be a pH-detector and may respond to changes in concentration of protons in an exemplary saliva sample. Herein, using three distinct compositions of an exemplary dye-based proton donor/acceptor in each respective sensing zone of sensing zones 118, 120, and 122 may lead to increase accuracy and selectivity of distinctive discoloration of chemical receptors 118*b*, 120*b*, and 122*b* due to interaction with saliva samples of distinct groups of healthy, cured, and COVID-19 infected individuals. In an exemplary embodiment, sensing zones 118, 120, and 122 may include three respective pH-sensitive organic dyes. In an exemplary embodiment, sensing zones 118, 120, and 122 may include three respective organic dyes with tri-aryl methane configuration. In an exemplary embodiment, an exemplary organic dye may include at least one of bromophenol red, bromocresol purple, and combinations thereof. In an exemplary embodiment, each sensing zone of sensing zones 118, 120, and 122 may include a respective mixture of at least one organic dye having tri-aryl methane configuration with at least one of DWES additive, phenylboronic acid (PBA) additive, and combinations thereof. In an exemplary embodiment, an exemplary mixture of an organic dye having tri-aryl methane configuration with DWES may be used to identify aldehyde and ketone species in an exemplary saliva sample. In an exemplary embodiment, an exemplary mixture of an organic dye having tri-aryl methane configuration with PBA may be used to identify diols (e.g. sugar) in an exemplary saliva sample. In an exemplary embodiment, each sensing zone of sensing zones 118, 120, and 122 may include a respective mixture of an exemplary additive in an exemplary organic dye with a relative concentration of additive to organic dye in a range of about 0.5 mol L$^{-1}$ to 3.5 mol L$^{-1}$. In an exemplary embodiment, each sensing zone of sensing zones 118, 120, and 122 may include a respective mixture of an exemplary additive in an exemplary organic dye dissolved in ethanol with a volume ratio of organic dye:additive in range of 3:1 to 5:1. In an exemplary embodiment, each sensing zone of sensing zones 118, 120, and 122 may include a respective mixture of an exemplary additive in an exemplary organic dye dissolved in ethanol with a volume ratio of organic dye:additive equal to 3:1. In an exemplary embodiment, sensing zone 118 may include a mixture of bromophenol red and DWES coated on individual area 118*a*. In an exemplary embodiment, sensing zone 120 may include a mixture of bromocresol purple and DWES coated on individual area 120*a*. In an exemplary embodiment, sensing zone 122 may include a mixture of bromocresol purple and PBA coated on individual area 122*a*.

Moreover, each sensing zone of sensing zones 124, 126, and 128 may include three different chemical receptors 124*b*, 126*b*, and 128*b* of at least one of a Lewis donor, a Lewis acceptor, and combinations thereof coated on three respective individual areas 124*a*, 126*a*, and 128*a*. In an exemplary embodiment, each sensing zone of sensing zones 124, 126, and 128 may include a respective porphyrin-based dye participating in a Lewis acid-base reaction with analytes in an exemplary saliva sample. In an exemplary embodiment, three different porphyrin-based dyes having different metal cores and different substitutions on structure of a respective porphyrin cage may be used in sensing zones 124, 126, and 128 leading to increase accuracy and selectivity of response of an exemplary group of Lewis donors/acceptors of chemical receptors to exemplary markers of COVID-19 in an exemplary saliva sample. In an exemplary embodiment, each sensing zone of sensing zones 124, 126, and 128 may include at least one of [meso-tetraphenylporphyrin]Iron (III) chloride (Fe(III)TPPCl), [meso-tetraphenylporphyrin]Tin (II) (Sn(II)TPP), meso-tetrakis(4-hydroxyphenyl) porphyrin-manganese (III) acetate (Mn(III)T(4-OH)PP(OAc)), and combinations thereof. In an exemplary embodiment, porphyrin-based dyes may recolor due to interaction with hydronium ions in an exemplary saliva sample. In an exemplary embodiment, each sensing zone of sensing zones 124, 126, and 128 may include a solution of at least one Lewis donor or at least one Lewis acceptor with a concentration in a range of 1.5 mg mL$^{-1}$ to 6.0 mg mL$^{-1}$ in Ethanol. In an exemplary embodiment, each sensing zone of sensing zones 124, 126, and 128 may include a solution of at least one Lewis donor or at least one Lewis acceptor with a concentration of 4.5 mg mL$^{-1}$ in Ethanol.

Additionally, each sensing zone of sensing zones 130, 132, and 134 may include at least one metal ion complex. In an exemplary embodiment, three distinct metal ion complexes may be used as chemical receptors 130*b*, 132*b*, and 134*b* coated on respective individual areas 130*a*, 132*a*, and 134*a*. In an exemplary embodiment, metal ion complex may include a metal ion chelated with a dye. In an exemplary embodiment, each sensing zone of sensing zones 130, 132, and 134 may include an exemplary metal ion complex prepared by forming a mixture containing a dye, a metal ion solution, and a buffer solution. In an exemplary embodiment, each sensing zone of sensing zones 130, 132, and 134 may include an exemplary mixture containing the same concentrations of an exemplary dye and an exemplary metal ion. In an exemplary embodiment, an exemplary dye may include an organic dye. In an exemplary embodiment, an exemplary dye may include a tri-aryl methane dye. In an exemplary embodiment, an exemplary dye may include pyrocatechol violet (Py). In an exemplary embodiment, an exemplary buffer solution may include a buffer solution with a pH value in a range of about 3.0 to 11. In an exemplary embodiment, an exemplary buffer solution may include a borate buffer solution with a concentration of about 0.1 M and pH of about 9.0. In an exemplary embodiment, an exemplary metal ion solution may include an aqueous solution of V (IV) ions, Fe (III) ions, Fe (II) ions, Cu (II) ions, Ni (II) ions, and combinations thereof. In an exemplary embodiment, concentrations of an exemplary dye and an exemplary metal ion solution may be adjusted at about 0.01 M in an exemplary mixture. In an exemplary embodiment, an exemplary metal ion complex may be formed in an exemplary mixture of an exemplary dye, an exemplary metal ion solution, and an exemplary buffer solution. In an exemplary embodiment, each sensing zone of sensing zones 130, 132, and 134 may include a solution of an exemplary metal ion complex with a concentration in a range of 0.005 mol $L^{-1}$ to 0.1 mol $L^{-1}$ in a buffer solution. In an exemplary embodiment, each sensing zone of sensing zones 130, 132, and 134 may include a solution of an exemplary metal ion complex with a concentration of 0.05 mol $L^{-1}$ in a buffer solution. In an exemplary embodiment, an exemplary metal ion complex including an exemplary tri-aryl methane dye and exemplary metal ions may be capable of sensing compounds containing acidic and amino groups in an exemplary saliva sample while interacting with exemplary detection zone 104. In detail, exemplary metal ions may have a high affinity to an analyte in an exemplary saliva sample for forming a complex with an exemplary analyte; thereby, resulting in releasing an exemplary organic dye from an exemplary metal ion complex structure and changing color of sensing zones 130, 132, and 134.

Figure 1D:
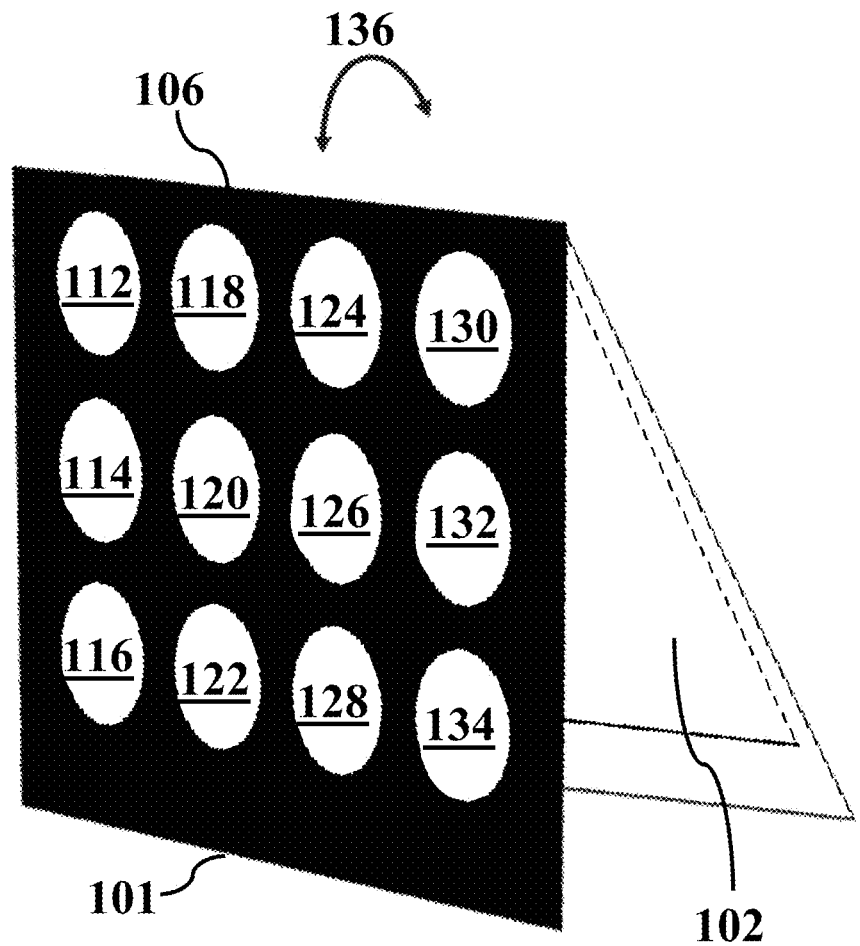
FIG. 1D illustrates a schematic view of an exemplary colorimetric sensor folding along an exemplary symmetric line, consistent with one or more exemplary embodiments of the present disclosure.

In an exemplary embodiment, an exemplary hydrophilic paper may be folded along a line, for example, hypothetical symmetric line 106 shown in FIG. 1D, between injection zone 102 and detection zone 104; allowing for putting injection zone 102 in contact with detection zone 104 and penetrating an exemplary saliva sample, injected on injection zone 102, from injection zone 102 to detection zone 104. In an exemplary embodiment, colorimetric sensor 100 may include a piece of an exemplary hydrophilic paper divided by a hypothetical symmetric line 106 of the piece of paper into two separate zones 102 and 104 separated by hydrophobic barrier 101 from each other. FIG. 1D illustrates a schematic view of exemplary colorimetric sensor 100 folding along symmetric line 106, consistent with one or more exemplary embodiments of the present disclosure. In an exemplary embodiment, colorimetric sensor 100 may be folded along exemplary symmetric line 106 in direction 136 allowing for putting injection zone 102 in contact with detection zone 104. In an exemplary embodiment, injection zone 102 may cover whole parts of array of 12 sensing zones 112 to 134 when colorimetric sensor 100 is folded along symmetric line 106. In an exemplary embodiment, an exemplary saliva sample may be dropped on injection zone 102. In an exemplary embodiment, an exemplary saliva sample may interact with array of 12 sensing zones 112 to 134 by penetrating an exemplary saliva sample from injection zone 102 into detection zone 104.

In an exemplary embodiment of the present disclosure, a method for fabrication of an exemplary colorimetric sensor may be described. In an exemplary embodiment, an exemplary fabrication method of an exemplary colorimetric sensor similar to colorimetric sensor 100 may include drawing a pre-determined pattern of colorimetric sensor 100 in an image-drawing software, printing the drawn pattern on an exemplary hydrophilic paper, forming exemplary hydrophobic barrier 101 by heating an exemplary hydrophilic paper with the pattern printed thereon in an oven, and coating exemplary array of chemical receptors 112b to 134b on respective array of individual areas 112a to 134a of detection zone 104 on an exemplary hydrophilic paper. In an exemplary embodiment, an exemplary pre-determined pattern may include an array of white circles corresponding to exemplary detection zone 104, a white rectangle corresponding to injection zone 102, and a black pattern of hydrophobic barrier 101. In an exemplary embodiment, the drawn pattern may be printed on an exemplary hydrophilic paper using a printer device. In an exemplary embodiment, exemplary hydrophobic barrier 101 may be formed by heating an exemplary hydrophilic paper with the pattern printed thereon at a temperature of about 200° C. in an oven for a time period of about 45 minutes. In an exemplary embodiment, heating an exemplary hydrophilic paper with the pattern printed thereon may lead to melting printing ink, penetrating printing ink into texture of an exemplary hydrophilic paper, and filling/blocking holes of an exemplary hydrophilic paper; thereby, resulting in forming hydrophobic sites on black printed sites of an exemplary printed pattern on an exemplary hydrophilic paper.

Figure 1E:
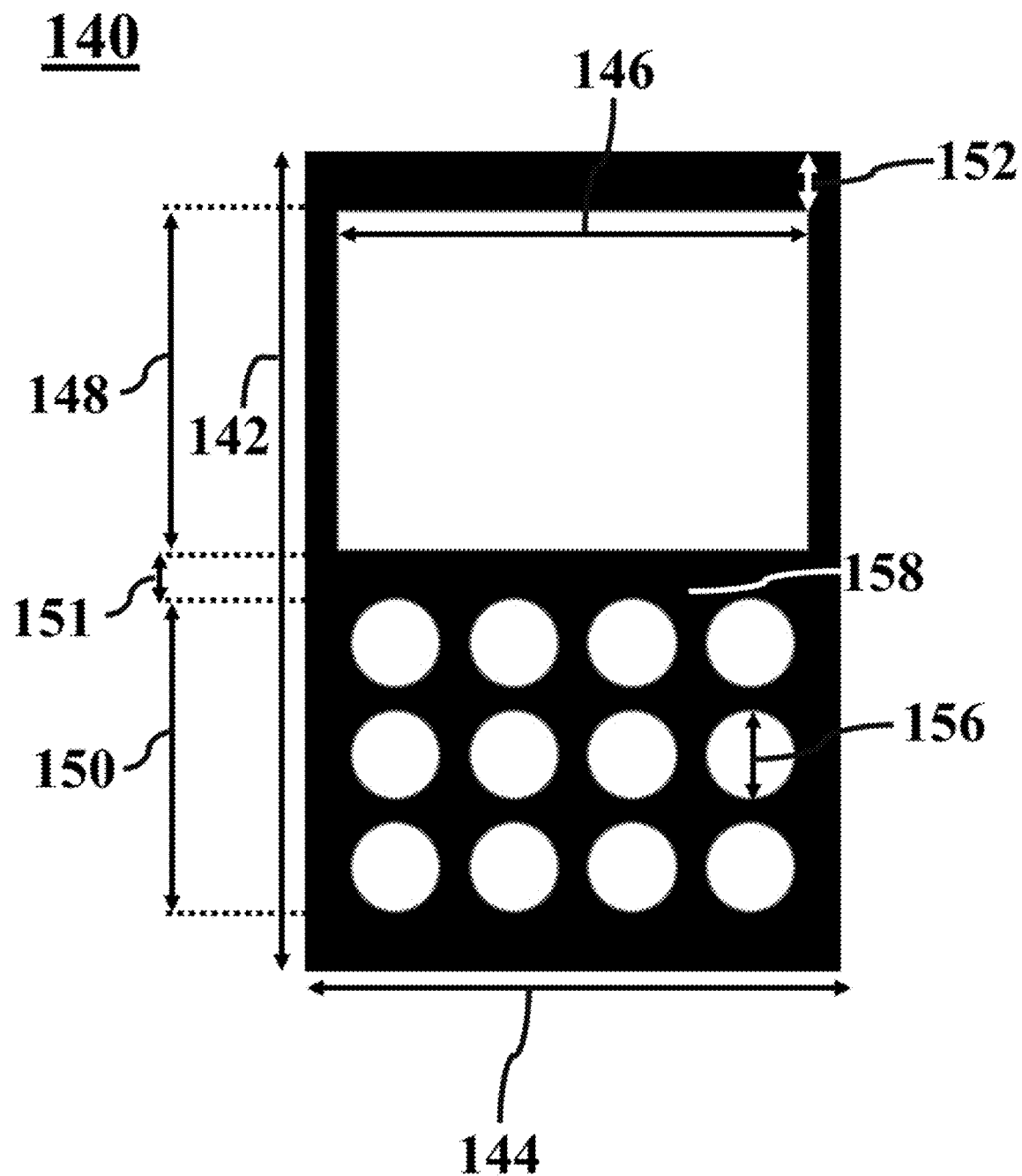
FIG. 1E illustrates an exemplary pattern of an exemplary colorimetric sensor, consistent with one or more exemplary embodiments of the present disclosure.

In an exemplary embodiment, drawing an exemplary pre-determined pattern of colorimetric sensor 100 may include drawing an arrangement of exemplary injection zone 102, exemplary array of individual areas 112a to 134a of exemplary detection zone 104, and exemplary hydrophobic barrier 101 with pre-determined dimensions. FIG. 1E illustrates an exemplary pattern 140 of exemplary colorimetric sensor 100, consistent with one or more exemplary embodiments of the present disclosure. In an exemplary embodiment, exemplary pattern 140 may be printed on a rectangular piece of an exemplary hydrophilic paper to form exemplary injection zone 102, hydrophobic barrier 101, and array of individual areas 112a to 134a of detection zone 104 of colorimetric sensor 100. Referring to FIG. 1E, an exemplary pattern 140 of exemplary colorimetric sensor 100 may include a rectangular shape with an exemplary length 142 of about 1.5 cm and an exemplary width 144 of about 1 cm. In an exemplary embodiment, an inner space of an exemplary rectangle may be divided into two rectangular zones with lengths of 148 and 150. In an exemplary embodiment, a first rectangular zone with length 148 and width 146 may form a pattern of exemplary injection zone 102 of FIGS. 1A, 1C, and 1D. In an exemplary embodiment, length 148 may be about 0.5 cm and width 146 may be about 0.8 cm. In an exemplary embodiment, a second rectangular zone with length 150 and width 146 may form a pattern of exemplary detection zone 104 of FIGS. 1A, 1C, and 1D. In an exemplary embodiment, exemplary detection zone 104 may include array of individual areas 112a to 134a (FIG. 1C), including an array of circular areas, with an exemplary diameter 156 of about 0.17 cm for each respective circular area. In an exemplary embodiment, array of individual areas 112a to 134a may include 12 circular areas arranged in three rows of four columns. In an exemplary embodiment, an exemplary distance 152 between an exemplary inner space and an exemplary outer space of an exemplary rectangular shape may be equal to about 0.1 cm. In an exemplary embodiment, an exemplary injection zone 102 and an exemplary detection zone 104 may be separated by a distance 151 of about 0.3 cm. In an exemplary embodiment, area 158 may include a pattern of a hydrophobic barrier 101. In an exemplary embodiment, area 158 may include an exemplary inner space of an exemplary rectangular shape except an exemplary injection zone 102 and an exemplary array of individual areas 112a to 134a of an exemplary detection zone 104.

In an additional step of an exemplary fabrication process of exemplary colorimetric sensor 100, exemplary designed pattern 140 may be printed on a hydrophilic paper using a printer device and exemplary injection zone 102 detection zone 104 may be formed on exemplary hydrophilic paper. Furthermore, an exemplary hydrophilic paper with printed pattern 140 thereon may be heated in an oven at a temperature of about 200° C. for about 45 minutes. In an exemplary embodiment, an exemplary heating process may melt hydrophobic printing ink at area 158 of printed pattern 140; allowing for penetrating hydrophobic printing ink into paper texture. Thereby, holes of an exemplary hydrophilic paper at area 158 may be filled with hydrophobic printing ink and exemplary area 158 may become completely hydrophobic, thereby, resulting in forming hydrophobic barrier 101. Furthermore, 12 chemical receptors as an exemplary array of chemical receptors 112b to 134b may be deposited/coated on respective array of individual areas 112a to 134a of exemplary detection zone 104; thereby, exemplary array of sensing zones 112 to 134 may be formed. In an exemplary embodiment, exemplary 12 chemical receptors may include 12 chemicals capable of changing their respective colors due to interaction with COVID-19 chemical markers in an exemplary saliva sample of a COVID-19 infected patient. In an exemplary embodiment, an exemplary paper may be folded along an exemplary symmetric line 106 illustrated in FIGS. 1A and 1D; allowing for putting exemplary injection zone 102 in contact with exemplary detection zone 104 by covering whole array of sensing zones 112 to 134 of exemplary detection zone 104 with exemplary injection zone 102. Thereby, when an exemplary saliva sample is injected on exemplary injection zone 102, an exemplary saliva sample may penetrate into array of sensing zones 112 to 134 of exemplary detection zone 104 and interact with respective deposited array of chemical receptors 112b to 134b thereon.

In an exemplary embodiment, coating exemplary array of chemical receptors 112b to 134b on respective array of individual areas 112a to 134a of detection zone 104 may include filling each respective individual area of individual areas 112a to 134a with a solution containing a respective chemical receptor of array of chemical receptors 112b to 134b. In an exemplary embodiment, coating an exemplary chemical receptor on each respective individual area may include filling a liquid-injecting instrument with a solution containing an exemplary chemical receptor and injecting the solution containing exemplary chemical receptor onto a respective individual area of an exemplary array of individual areas 112a to 134a of detection zone 104. In an exemplary embodiment, the liquid-injecting instrument may include a syringe, a micropipette, and combinations thereof.

Figure 1F:
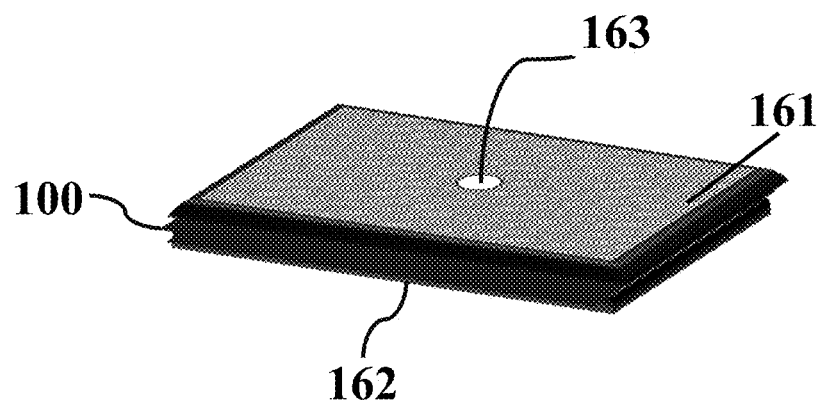
FIG. 1F illustrates a schematic view of an exemplary colorimetric sensing package including an exemplary colorimetric sensor fixed between two exemplary planar sheets, consistent with one or more exemplary embodiments of the present disclosure.
Figure 1G:
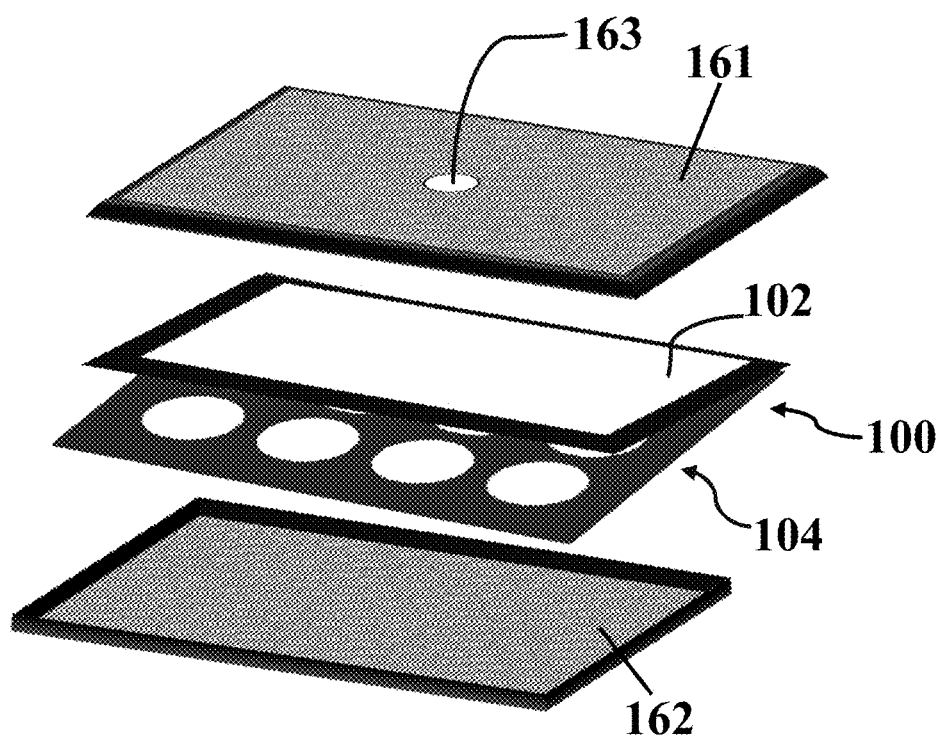
FIG. 1G illustrates an exploded view of an exemplary colorimetric sensing package, consistent with one or more exemplary embodiments of the present disclosure.

In an exemplary embodiment of the present disclosure, exemplary colorimetric sensor 100 may be fixed firmly inside two holding sheets; allowing for a firm contact between exemplary injection zone 102 and exemplary detection zone 104. FIG. 1F illustrates a schematic view of a colorimetric sensing package 160 including exemplary colorimetric sensor 100 fixed between two planar sheets 161 and 162, consistent with one or more exemplary embodiments of the present disclosure. In an exemplary embodiment, exemplary colorimetric sensor 100 may be fixed between two planar sheets 161 and 162 with an injection site 163 embedded in planar sheet 161. In an exemplary embodiment, injection site 163 may include a hole in planar sheet 161; allowing for an access to injection zone 102 for injecting an exemplary saliva sample thereon. In an exemplary embodiment, two planar sheets 161 and 162 may include two respective sheets made of poly(methyl methacrylate) (PMMA). FIG. 1G illustrates an exploded view of colorimetric sensing package 160, consistent with one or more exemplary embodiments of the present disclosure. In an exemplary embodiment, colorimetric sensor 100 may be folded so that injection zone 102 may cover whole parts of detection zone 104. In an exemplary embodiment, exemplary folded colorimetric sensor 100 may be placed between two planar sheets 161 and 162 so that planar sheet 161 may be fixed on an outer surface of injection zone 102 and planar sheet 162 may be fixed on an outer surface of detection zone 104. In an exemplary embodiment, injection site 163 may include a hole embedded in the middle of planar sheet 161. In an exemplary embodiment, an exemplary saliva sample may be injected through injection site 163 on injection zone 102; thereby, an exemplary saliva sample may vertically penetrate from injection zone 102 into detection zone 104. It should be noted that saliva samples may not move at the same flow rates on a paper substrate with two-dimensional structures (e.g., microfluidic, lateral flow, and distance-based formats) due to different viscosities of different saliva samples. However, an origami structure of colorimetric sensor 100 may provide overlapping injection zone 102 and detection zone 104 by folding colorimetric sensor 100; allowing for penetrating species of an exemplary saliva sample vertically into paper texture, thereby, resulting in shorter test time and needing low volume of an exemplary saliva sample.

Figure 2:
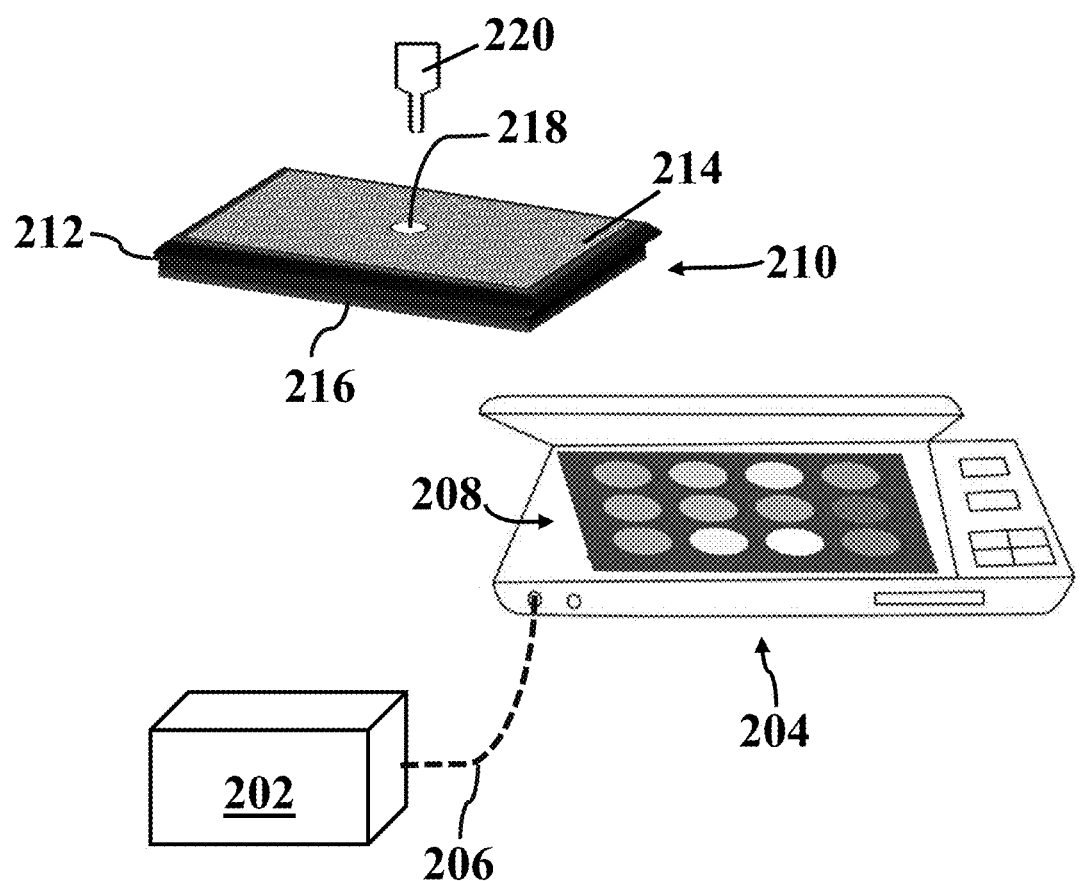
FIG. 2 shows a schematic view of an exemplary system for detecting COVID-19 infection, consistent with one or more exemplary embodiments of the present disclosure.

In an exemplary embodiment of the present disclosure, an exemplary colorimetric sensor and/or an exemplary colorimetric sensing package may be utilized in a system for detecting COVID-19 infection using an exemplary saliva sample acquired form a person suspected to be infected by COVID-19 virus. FIG. 2 shows a schematic view of an exemplary system 200 for detecting COVID-19 infection, consistent with one or more exemplary embodiments of the present disclosure. Exemplary system 200 may include a processing unit 202, an image-capturing device 204, a colorimetric sensing package 210 similar to exemplary colorimetric sensing package 160 illustrated in FIGS. 1F and 1G, and a sample-injecting instrument 220.

In an exemplary embodiment, sample-injecting instrument 220 may comprise a syringe, a micropipette, and combinations thereof. In an exemplary embodiment, sample-injecting instrument 220 may be configured to be filled with an exemplary saliva sample and inject an exemplary saliva sample on exemplary colorimetric sensor 212 using thereof. In an exemplary embodiment, an exemplary saliva sample may be acquired from a person who is suspected to be infected by COVID-19 virus. In an exemplary embodiment, colorimetric sensing package 210 may include an exemplary colorimetric sensor 212 similar to colorimetric sensor 100 illustrated in FIGS. 1A-1G, two planar sheets 214 and 216 similar to two planar sheets 161 and 162 illustrated in FIGS. 1F and 1G, and injection site 218 similar to injection site 163 illustrated in FIGS. 1F and 1G. In an exemplary embodiment, colorimetric sensing package 210 may be configured to inject an exemplary saliva sample through injection site 218 on an exemplary injection zone (not illustrated in FIG. 2) of colorimetric sensor 212; thereby, leading to interacting an exemplary saliva sample with exemplary detection zone 208 of colorimetric sensor 212. In an exemplary embodiment, detection zone 208 may be similar to detection zone 104 of colorimetric sensor 100. In an exemplary embodiment, an interaction between an exemplary saliva sample and exemplary detection zone 208 may lead to color changes of one or more chemical receptor coated on respective one or more sensing zone of an exemplary array of sensing zones of detection zone 208. In an exemplary embodiment, image-capturing device 204 may be configured to capture an image from detection zone 208 after injection of an exemplary saliva sample on colorimetric sensor 212. In an exemplary embodiment, image-capturing device 204 may be further configured to capture an image from detection zone 208 before injection of an exemplary saliva sample on colorimetric sensor 212. In an exemplary embodiment, image-capturing device 204 may be electrically connected to processing unit 202 via an electrically connection instrument 206. In an exemplary embodiment, electrically connection instrument 206 may include a wireless electrical connector or an electrically conductive wire. In an exemplary embodiment, image-capturing device 204 may be electrically connected to processing unit 202 using a wireless electrical connection utilizing Bluetooth modules embedded in processing unit 202 and image-capturing device 204. In an exemplary embodiment, image-capturing device 204 may be electrically connected to processing unit 202 using an electrically conductive wire. In an exemplary embodiment, image-capturing device 204 may include at least one of a camera, a digital camera, a camera of a cellphone, a scanner, and a paper-based document scanner. In an exemplary embodiment, processing unit 202 may be configured to receive a captured image of detection zone 208 form image-capturing device 204 and detecting a COVID-19 infection by analyzing an exemplary captured image. In an exemplary embodiment, processing unit 202 may include a memory having processor-readable instructions stored therein and a processor. An exemplary processor may be configured to access the memory and execute the processor-readable instructions. In an exemplary embodiment, the processor may be configured to perform a method by executing the processor-readable instructions. In an exemplary embodiment, an exemplary method may include one or more steps of an exemplary method described herein below for detecting COVID-19 infection of a person using an exemplary saliva sample acquired from the person.

Figure 3:
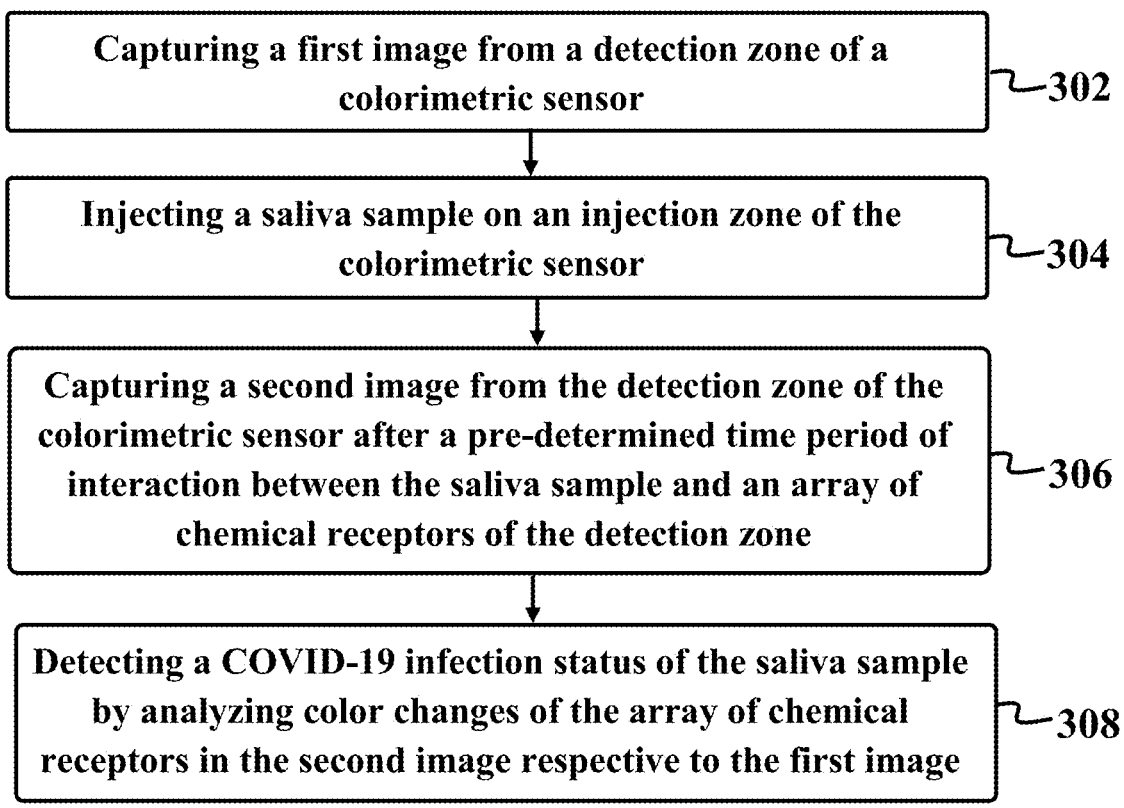
FIG. 3 shows a flowchart of an exemplary method for detecting COVID-19 infection using an exemplary saliva sample acquired from a person who is suspected to be infected by COVID-19 virus, consistent with one or more exemplary embodiments of the present disclosure.

In an exemplary embodiment, the present disclosure describes an exemplary method for detecting COVID-19 infection. In an exemplary embodiment, an exemplary method may include detecting COVID-19 infection status of a person by analyzing an exemplary saliva sample acquired from the person using an exemplary colorimetric sensor similar to sensors 100 and 212. FIG. 3 shows a flowchart of an exemplary method 300 for detecting COVID-19 infection using an exemplary saliva sample acquired from a person who is suspected to be infected by COVID-19 virus, consistent with one or more exemplary embodiments of the present disclosure. Exemplary method 300 may include capturing a first image from a detection zone of a colorimetric sensor (step 302), injecting a saliva sample on an injection zone of an exemplary colorimetric sensor (step 304), capturing a second image from an exemplary detection zone of an exemplary colorimetric sensor after a pre-determined time period of interaction between an exemplary saliva sample and an array of chemical receptors of an exemplary detection zone (step 306), and detecting a COVID-19 infection status of an exemplary saliva sample by analyzing color changes of an exemplary array of chemical receptors in the second image respective to the first image (step 308). In an exemplary embodiment, exemplary method 300 may be carried out utilizing exemplary system 200 described herein above. In an exemplary embodiment, exemplary steps of method 300 are described in further detail below in context of exemplary system 200.

In further detail with respect to step 302, step 302 may include capturing a first image from a detection zone of a colorimetric sensor. In an exemplary embodiment, an exemplary first image may be captured from detection zone 208 of colorimetric sensor 212 using image-capturing device 204 before injecting an exemplary saliva sample on an exemplary injection zone of colorimetric sensor 212.

In further detail with respect to step 304, step 304 may include injecting an exemplary saliva sample on an exemplary injection zone of an exemplary colorimetric sensor similar to colorimetric sensors 100 or 212 described herein above. In an exemplary embodiment, injecting an exemplary saliva sample on an exemplary injection zone of an exemplary colorimetric sensor may include acquiring an exemplary saliva sample from a person suspected to be infected with COVID-19 virus, covering an exemplary injection zone of an exemplary colorimetric sensor on an exemplary detection zone of an exemplary colorimetric sensor by folding an exemplary colorimetric sensor, forming an exemplary colorimetric sensing package similar to colorimetric sensing package 160 by putting an exemplary folded colorimetric sensor firmly inside two exemplary planar holders similar to planar holders 161 and 162, injecting an exemplary saliva sample on an exemplary injection zone through an exemplary injection site similar to injection site 163, and incubating an exemplary saliva sample with an exemplary array of chemical receptors of an exemplary detection zone by retaining an exemplary colorimetric sensing package at an ambient temperature for a pre-determined period of time.

In an exemplary embodiment, injecting an exemplary saliva sample on an exemplary injection zone of an exemplary colorimetric sensor may further include penetrating an exemplary saliva sample from an exemplary injection zone to an exemplary detection zone and interacting an exemplary saliva sample with an exemplary array of chemical receptors during a pre-determined period of time in a range of at least 4 minutes. In an exemplary embodiment, an exemplary pre-determined period of time may be in a range of 4 minutes to 10 minutes. In an exemplary embodiment, color of one or more chemical receptors of an exemplary array of chemical receptors may change due to an interaction between an exemplary saliva sample and an exemplary array of chemical receptors.

In further detail with respect to step 306, step 306 may include capturing a second image from an exemplary detection zone of an exemplary colorimetric sensor after an exemplary pre-determined time period of interaction between an exemplary saliva sample and an array of chemical receptors of an exemplary detection zone. In an exemplary embodiment, an exemplary second image may be captured from detection zone 208 of colorimetric sensor 212 using image-capturing device 204 after incubation of an exemplary injected saliva sample with an exemplary array of chemical receptors of detection zone 208 of colorimetric sensor 212.

In further detail with respect to step 308, step 308 may include detecting a COVID-19 infection status of an exemplary saliva sample by analyzing color changes of an exemplary array of chemical receptors in an exemplary second image respective to an exemplary first image. In an exemplary embodiment, detecting COVID-19 infection status of an exemplary saliva sample by analyzing color changes of an exemplary array of chemical receptors in an exemplary second image respective to an exemplary first image (step 308) may include comparing color changes of an exemplary array of chemical receptors in an exemplary second image respective to an exemplary first image with color changes of an exemplary array of chemical receptors in a plurality of images with known COVID-19 infection status respective to an exemplary first image. In an exemplary embodiment, the plurality of images with known COVID-19 infection status may include three sets of images associated with three groups of people with known COVID-19 infection status. In an exemplary embodiment, the three sets of images may include a first set of images associated with a respective plurality of COVID-19 infected individuals, a second set of images associated with a respective plurality of healthy individuals, and a third set of images associated with a respective plurality of cured individuals after a COVID-19 infection. In an exemplary embodiment, each image of the plurality of images with known COVID-19 infection status may be captured and recorded after injecting an exemplary saliva sampled acquired from each respective individual of people with known COVID-19 infection status.

In more details with respect to step 308, detecting COVID-19 infection status of an exemplary saliva sample (step 308) may further include one of detecting an exemplary saliva sample being acquired from a COVID-19 infected patient, detecting an exemplary saliva sample being acquired from a healthy individual, and detecting an exemplary saliva sample being acquired from a cured individual after a COVID-19 infection. In an exemplary embodiment, detecting COVID-19 infection status of an exemplary saliva sample (step 308) may include detecting that an exemplary saliva sample is acquired from a COVID-19 infected patient if color changes of an exemplary array of chemical receptors in an exemplary second image respective to an exemplary first image is similar to color changes of an exemplary array of chemical receptors in exemplary first set of images associated with the respective plurality of COVID-19 infected individuals respective to an exemplary first image. A "similarity" between color changes of an exemplary array of chemical receptors in an exemplary second image respective to an exemplary first image and color changes of an exemplary array of chemical receptors in an exemplary first set of images may refer to detecting discoloration of identical chemical receptors of an exemplary array of chemical receptors in an exemplary second image and an exemplary first set of images. In an exemplary embodiment, detecting COVID-19 infection status of an exemplary saliva sample may include detecting an exemplary saliva sample is acquired from a COVID-19 infected patient if color of Bromophenol red+DWES, Bromocresol purpule+DWES, Fe(III)TPPCL, Fe(II)-Py, and Cu(II)-Py is changed in an exemplary second image respective to an exemplary first image. In an exemplary embodiment, detecting COVID-19 infection status of an exemplary saliva sample (step 308) may include detecting that an exemplary saliva sample is acquired from a healthy individual if color changes of an exemplary array of chemical receptors in an exemplary second image respective to an exemplary first image is similar to color changes of an exemplary array of chemical receptors in exemplary second set of images associated with the respective plurality of healthy individuals respective to an exemplary first image. A "similarity" between color changes of an exemplary array of chemical receptors in an exemplary second image respective to an exemplary first image and color changes of an exemplary array of chemical receptors in an exemplary second set of images may refer to detecting discoloration of identical chemical receptors of an exemplary array of chemical receptors in an exemplary second image and an exemplary second set of images. In an exemplary embodiment, detecting COVID-19 infection status of an exemplary saliva sample may include detecting an exemplary saliva sample is acquired from a healthy individual if color of CA-AuNPs, Mn(III)T(4-OH)PP(OAc), V(IV)-Py, Fe(II)-Py, and Cu(II)-Py is changed in an exemplary second image respective to an exemplary first image. In an exemplary embodiment, detecting COVID-19 infection status of an exemplary saliva sample (step 308) may include detecting that an exemplary saliva sample is acquired from a cured individual after a COVID-19 infection if color changes of an exemplary array of chemical receptors in an exemplary second image respective to an exemplary first image is similar to color changes of an exemplary array of chemical receptors in exemplary third set of images associated with the respective plurality of cured individuals respective to an exemplary first image. A "similarity" between color changes of an exemplary array of chemical receptors in an exemplary second image respective to an exemplary first image and color changes of an exemplary array of chemical receptors in an exemplary third set of images may refer to detecting discoloration of identical chemical receptors of an exemplary array of chemical receptors in an exemplary second image and an exemplary third set of images. In an exemplary embodiment, detecting COVID-19 infection status of an exemplary saliva sample may include detecting an exemplary saliva sample is acquired from a cured individual if color of Fe(III)TPPCL, V(IV)-Py, Fe(II)-Py, and Cu(II)-Py is changed in an exemplary second image respective to an exemplary first image.

In an exemplary embodiment, detecting COVID-19 infection status of an exemplary saliva sample by analyzing color changes of an exemplary array of chemical receptors in an exemplary second image respective to an exemplary first image (step 308) may include extracting an array of color values of each chemical receptor in exemplary first and second images, generating color value vectors respective to exemplary first and second images, generating a difference color value vector using color value vectors of exemplary first and second images, analyzing exemplary difference color value vector in comparison with a plurality of difference color value vectors formed for an exemplary respective plurality of images with known COVID-19 infection status, and detecting COVID-19 infection status of an exemplary saliva sample based on a similarity of an exemplary difference color value vector associated with exemplary saliva sample with exemplary difference color value vectors associated with one group of three groups of people with known COVID-19 infection status. In an exemplary embodiment, analyzing exemplary difference color value vector in comparison with a plurality of difference color value vectors may be carried out using a principle component analysis-linear discriminate analysis (PCA-DA) technique.

Figure 4:
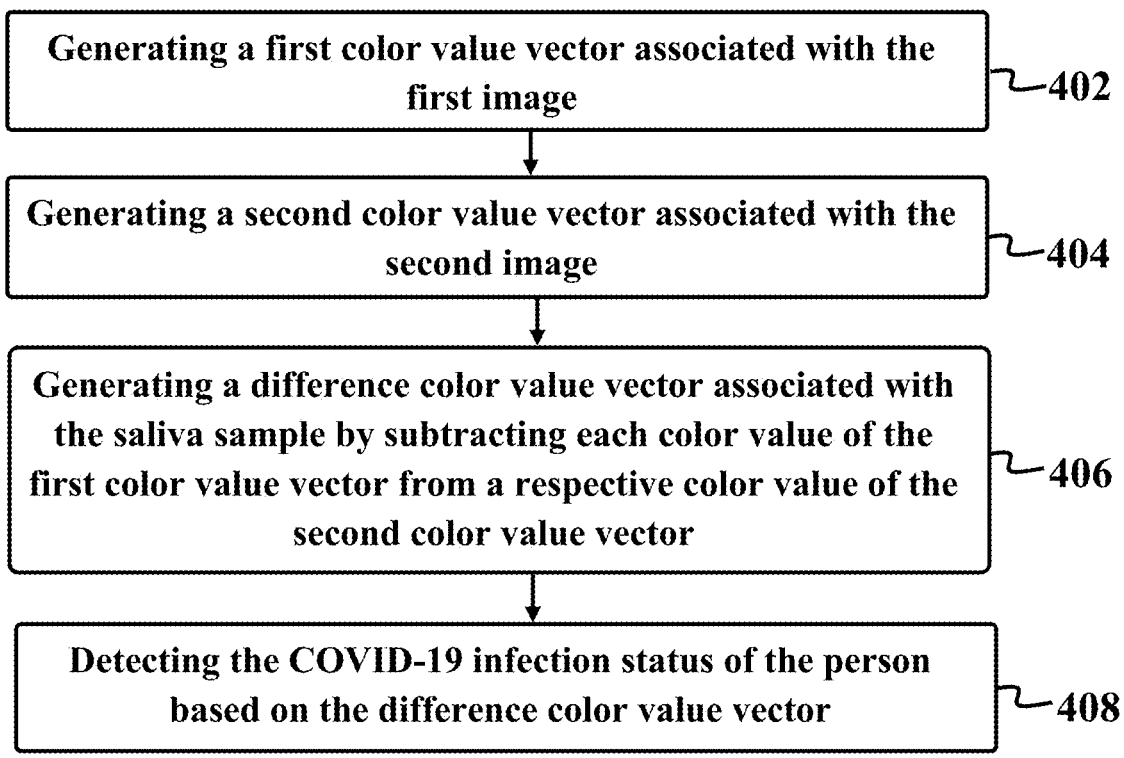
FIG. 4 shows a flowchart of an exemplary method for detecting COVID-19 infection status of an exemplary saliva sample by analyzing color changes of an exemplary array of chemical receptors in an exemplary second image respective to an exemplary first image, consistent with one or more exemplary embodiments of the present disclosure.

In an exemplary embodiment of the present disclosure, an exemplary method is described for detecting COVID-19 infection status of an exemplary saliva sample by analyzing color changes of an exemplary array of chemical receptors in an exemplary second image respective to an exemplary first image (step 308) based on generating and utilizing an exemplary difference color value vector using an exemplary first image and an exemplary second image. FIG. 4 shows a flowchart of an exemplary method 400 for detecting COVID-19 infection status of an exemplary saliva sample by analyzing color changes of an exemplary array of chemical receptors in an exemplary second image respective to an exemplary first image (step 308), consistent with one or more exemplary embodiments of the present disclosure. In an exemplary embodiment, exemplary method 400 may include generating a first color value vector associated with an exemplary first image (step 402), generating a second color value vector associated with an exemplary second image (step 404), generating a difference color value vector associated with an exemplary saliva sample by subtracting each color value of an exemplary first color value vector from a respective color value of an exemplary second color value vector (step 406), and detecting a COVID-19 infection status of an exemplary person based on an exemplary difference color value vector (step 408).

In further detail with respect to step 402, step 402 may include generating a first color value vector associated with an exemplary first image. In an exemplary embodiment, an exemplary first color value vector may include a first array of a respective first set of three numerical color values of three respective color components of color of each respective chemical receptor of an exemplary array of chemical receptors in an exemplary first image. In an exemplary embodiment, exemplary three color components may include red, green, and blue. In an exemplary embodiment, generating an exemplary first color value vector may include extracting color values of blue, green, and red associated with each chemical receptor in an exemplary first image and forming an exemplary first array of exemplary respective first sets of extracted three color values respective to an exemplary array of chemical receptors. In an exemplary embodiment, extracting color values of blue, green, and red may be done using an image processing technique utilizing one or more processors. In an exemplary embodiment, an exemplary first color value vector may be formed utilizing one or more processors. In an exemplary embodiment, an exemplary first color may be formed using a relation defined by Equation 1 as follows:

$$V_1=[R_{11}G_{11}B_{11}\ldots R_{i1}G_{i1}B_{i1}\ldots R_{n1}G_{n1}B_{n1}]$$ Equation 1

Where, $R_{i1}$ is red component value of color of $i^{th}$ chemical receptor of an exemplary array of chemical receptors in an exemplary first image, $G_{i1}$ is green component value of color of $i^{th}$ chemical receptor of an exemplary array of chemical receptors in an exemplary first image, $B_{i1}$ is blue component value of color of $i^{th}$ chemical receptor of an exemplary array of chemical receptors in an exemplary first image, and n is total number of chemical receptors of an exemplary array of chemical receptors.

In further detail with respect to step 404, step 404 may include generating a second color value vector associated with an exemplary second image. In an exemplary embodiment, an exemplary second color value vector may include a second array of a respective second set of three numerical color values of three respective color components of color of each respective chemical receptor of an exemplary array of chemical receptors in an exemplary second image. In an exemplary embodiment, exemplary three color components may include red, green, and blue. In an exemplary embodiment, generating an exemplary second color value vector may include extracting color values of blue, green, and red associated with each chemical receptor in an exemplary second image and forming an exemplary second array of exemplary respective second sets of extracted three color values respective to an exemplary array of chemical receptors. In an exemplary embodiment, extracting color values of blue, green, and red may be done using an image processing technique utilizing one or more processors. In an exemplary embodiment, an exemplary second color value vector may be formed utilizing one or more processors. In an exemplary embodiment, an exemplary second color may be formed using a relation defined by Equation 2 as follows:

$$V_2=[R_{12}G_{12}B_{12}\ldots R_{i2}G_{i2}B_{i2}\ldots R_{n2}G_{n2}B_{n2}]$$ Equation 2

Where, $R_{i2}$ is red component value of color of $i^{th}$ chemical receptor of an exemplary array of chemical receptors in an exemplary second image, $G_{i2}$ is green component value of color of $i^{th}$ chemical receptor of an exemplary array of chemical receptors in an exemplary second image, $B_{i2}$ is blue component value of color of $i^{th}$ chemical receptor of an exemplary array of chemical receptors in an exemplary second image, and n is total number of chemical receptors of an exemplary array of chemical receptors.

In further detail with respect to step 406, step 406 may include generating a difference color value vector associated with an exemplary saliva sample by subtracting each color value of an exemplary first color value vector from a respective color value of an exemplary second color value vector. In an exemplary embodiment, an exemplary difference color value vector may be calculated using Equation 3 as follows:

$$\Delta V = V_2 - V_1 = [\Delta R_1 \Delta G_1 \Delta B_1 \ldots \Delta R_i \Delta G_i \Delta B_i \ldots \Delta R_n \Delta G_n \Delta B_n],$$ Equation 3

Where, $\Delta R_i$, $\Delta G_i$, and $\Delta B_i$ is defined by respective Equations 4 to 6 as follows:

$$\Delta R_i = R_{i2} - R_{i1}$$ Equation 4

$$\Delta G_i = G_{i2} - G_{i1}$$ Equation 5

$$\Delta B_i = B_{i2} - B_{i1}$$ Equation 6

In further detail with respect to step 408, step 408 may include detecting COVID-19 infection status of an exemplary person based on an exemplary difference color value vector. In an exemplary embodiment, detecting COVID-19 infection status of an exemplary person based on an exemplary difference color value vector may include comparing each element of the difference color value vector with a respective element of three reference difference color value vectors and detecting the person is one of a COVID-19 infected patient, a healthy individual, or a cured individual after a COVID-19 infection. In an exemplary embodiment, the three reference difference color value vectors may include a first mean difference color value vector of a first plurality of difference color value vectors generated for a first respective plurality of saliva samples acquired from a respective plurality of COVID-19 patients, a second mean difference color value vector of a second plurality of difference color value vectors generated for a second respective plurality of saliva samples acquired from a respective plurality of healthy individuals, and a third mean difference color value vector of a third plurality of difference color value vectors generated for a third respective plurality of saliva samples acquired from a respective plurality of cured individuals after a COVID-19 infection. In an exemplary embodiment, detecting the person is one of a COVID-19 infected patient, a healthy individual, or a cured individual after a COVID-19 infection may include detecting the person is infected by COVID-19 virus if a difference percentage between each element of the difference color value vector and the respective element of the first reference difference color value vector is less than 5%. In an exemplary embodiment, detecting the person is one of a COVID-19 infected patient, a healthy individual, or a cured individual after a COVID-19 infection may include detecting the person is healthy if a difference percentage between each element of the difference color value vector and the respective element of the second reference difference color value vector is less than 5%. In an exemplary embodiment, detecting the person is one of a COVID-19 infected patient, a healthy individual, or a cured individual after a COVID-19 infection may include detecting the person is cured after a COVID-19 infection if a difference percentage between each element of the difference color value vector and the respective element of the third reference difference color value vector is less than 5%. As used herein, a "difference percentage" between two values may include a relative difference of a first value of the two values to a second value of the two values.

In an exemplary embodiment, exemplary method 300 may further include generating the three reference difference color value vectors. In an exemplary embodiment, generating the three reference difference color value vectors may include generating three pluralities of difference color value vectors associated with three respective pluralities of saliva samples acquired from three respective groups and forming a respective reference difference color value vector for each plurality of difference color value vectors of three pluralities of difference color value vectors by calculating an average of respective elements of each plurality of difference color value vectors. In an exemplary embodiment, the three groups may include a plurality of COVID-19 patients, a plurality of healthy individuals, and a plurality of cured individuals after a COVID-19 infection.

In an exemplary embodiment, generating each plurality of difference color value vectors of three pluralities of difference color value vectors may include preparing an exemplary first image and an exemplary second image for each exemplary saliva sample of each exemplary plurality of saliva samples acquired from each exemplary respective plurality of people in the three groups by applying steps 302 to 306 of exemplary method 300 to each exemplary saliva sample of an exemplary plurality of saliva samples acquired from an exemplary respective plurality of people and generating a difference color value vector for each exemplary saliva sample using a process including steps 402 to 406 of exemplary method 400. In an exemplary embodiment, an exemplary reference difference color value vector ($\Delta V_R$) may be generated using a relation defined by Equation 7 as follows:

$$\Delta V_R = \left[ \frac{\sum_{i=1}^{P} \Delta R_1}{P} \frac{\sum_{i=1}^{P} \Delta G_1}{P} \frac{\sum_{i=1}^{P} \Delta B_1}{P} \cdots \frac{\sum_{i=1}^{P} \Delta R_i}{P} \right. \qquad \text{Equation 7}$$

$$\left. \frac{\sum_{i=1}^{P} \Delta G_i}{P} \frac{\sum_{i=1}^{P} \Delta B_i}{P} \cdots \frac{\sum_{i=1}^{P} \Delta R_n}{P} \frac{\sum_{i=1}^{P} \Delta G_n}{P} \frac{\sum_{i=1}^{P} \Delta B_n}{P} \right],$$

Where, P is total number of people of an exemplary plurality of people in a respective group of the three groups.

In an exemplary embodiment, detecting COVID-19 infection status of an exemplary person based on an exemplary difference color value vector may include calculating a magnitude of an exemplary difference color value vector and detecting COVID-19 infection status of an exemplary person by comparing the magnitude of an exemplary difference color value vector with a threshold value. In an exemplary embodiment, calculating the magnitude of an exemplary difference color value vector may be done using a relation defined by Equation 8 as follows:

$$|\Delta V| = \sqrt{\sum_{i=1}^{n}((\Delta R_i)^2 + (\Delta G_i)^2 + (\Delta B_i)^2)} \qquad \text{Equation 8}$$

Where, $|\Delta V|$ is magnitude of an exemplary difference color value vector.

In an exemplary embodiment, the threshold value may include a borderline value between a first range of magnitudes of an exemplary plurality of difference color value vectors associated with an exemplary respective plurality of COVID-19 patients and a second range of magnitudes of a plurality of difference color value vectors associated with a respective plurality of healthy individuals. In an exemplary embodiment, the threshold value may include an average of magnitudes of an exemplary plurality of difference color value vectors associated with an exemplary respective plurality of COVID-19 patients. In an exemplary embodiment, detecting the COVID-19 infection status of an exemplary person may include detecting an exemplary person is healthy if the magnitude of an exemplary difference color value vector is more than an exemplary threshold value or detecting an exemplary person is COVID-19 infected if the magnitude of an exemplary difference color value vector is less than an exemplary threshold value. In an exemplary embodiment, an exemplary threshold value may include a value of about 342.4. In an exemplary embodiment, an exemplary person is healthy if the magnitude of an exemplary difference color value vector is more than about 342.4. In an exemplary embodiment, an exemplary person is a COVID-19 infected patient if the magnitude of an exemplary difference color value vector is less than about 342.4.

Referring again to FIG. 3, in further detail with respect to step 308, detecting COVID-19 infection status of an exemplary saliva sample by analyzing color changes of an exemplary array of chemical receptors in an exemplary second image respective to an exemplary first image may include detecting an exemplary person is infected by COVID-19 virus if a change in color of at least two COVID-19 indicative chemical receptors is detected in the second image respective to the first image. In an exemplary embodiment, the at least two COVID-19 indicative chemical receptors may include two pH-sensitive organic dyes. In an exemplary embodiment, the at least two COVID-19 indicative chemical receptors may include a first pH-sensitive organic dye and a second pH-sensitive organic dye. In an exemplary embodiment, the first pH-sensitive organic dye may include a mixture of bromophenol red and DWES in ethanol with a volume ratio of bromophenol red:additive equal to 3:1. In an exemplary embodiment, the second pH-sensitive organic dye may include a mixture of bromocresol purple and DWES in ethanol with a volume ratio of bromophenol red:additive equal to 3:1.

In an exemplary embodiment, detecting COVID-19 infection status of an exemplary saliva sample (step 308) may further include detecting a severity grade of COVID-19 infection of an exemplary person. In an exemplary embodiment, detecting a severity grade of COVID-19 infection of an exemplary person may include extracting two sets of three numerical color values of the second pH-sensitive organic dye in the first image and the second image, generating a difference color value vector associated with the second pH-sensitive organic dye by subtracting the two sets of three numerical color values from each other, calculating a magnitude of discoloration of the second pH-sensitive organic dye in the second image respective to the first image, and detecting severity grade of COVID-19 infection of an exemplary person based on the calculated magnitude of discoloration of the second pH-sensitive organic dye in the second image respective to the first image. In an exemplary embodiment, the three numerical color values may include respective values of three color components of color of the second pH-sensitive organic dye. In an exemplary embodiment, the three color components may include red, green, and blue.

In an exemplary embodiment, calculating the magnitude of discoloration of the second pH-sensitive organic dye in the second image respective to the first image may include calculating magnitude of the difference color value vector associated with the second pH-sensitive organic dye. In an exemplary embodiment, the magnitude of the difference color value vector associated with the second pH-sensitive organic dye may be calculated using a relation defined by Equation 9 as follows:

$$|\Delta V| = \sqrt{(\Delta R)^2 + (\Delta G)^2 + (\Delta B)^2} \quad \text{Equation 9}$$

Where, $|\Delta V|$ is the magnitude of discoloration of the second pH-sensitive organic dye, $\Delta R$ is a difference between respective red color values in the first image and the second image, $\Delta G$ is a difference between respective green color values in the first image and the second image, and $\Delta B$ is a difference between respective blue color values in the first image and the second image.

In an exemplary embodiment, detecting the severity grade of COVID-19 infection of an exemplary person based on the calculated magnitude of discoloration of the second pH-sensitive organic dye in the second image respective to the first image may include one of detecting an exemplary person is mildly infected by COVID-19 virus, detecting an exemplary person is moderately infected by COVID-19 virus, detecting an exemplary person is severely infected by COVID-19 virus, and detecting an exemplary person is highly-severe infected by COVID-19 virus. In an exemplary embodiment, detecting the severity grade of COVID-19 infection of an exemplary person may include detecting the person is mildly infected by COVID-19 virus if the magnitude of discoloration of the second pH-sensitive organic dye is in a range of 0 to 150. In an exemplary embodiment, a mildly infection by COVID-19 virus may include a cycle threshold (CT) number in a range of 28 to 32. In an exemplary embodiment, an exemplary CT number may include a CT number for N gene obtained in a polymerase-chain-reaction (PCR) test applied to an exemplary person. In an exemplary embodiment, detecting the severity grade of COVID-19 infection of an exemplary person may include detecting the person is moderately infected by COVID-19 virus if the magnitude of discoloration of the second pH-sensitive organic dye is in a range of 150 to 160. In an exemplary embodiment, a moderately infection by COVID-19 virus may include a CT number in a range of 23 to 27. In an exemplary embodiment, detecting the severity grade of COVID-19 infection of an exemplary person may include detecting the person is severely infected by COVID-19 virus if the magnitude of discoloration of the second pH-sensitive organic dye is in a range of 160 to 180. In an exemplary embodiment, a severely infection by COVID-19 virus may include a CT number in a range of 18 to 22. In an exemplary embodiment, detecting the severity grade of COVID-19 infection of an exemplary person may include detecting the person is highly-severe infected by COVID-19 virus if the magnitude of discoloration of the second pH-sensitive organic dye is in a range of 180 to 220. In an exemplary embodiment, a highly-severe infection by COVID-19 virus may include a CT number in a range of 15 to 17.

In an exemplary embodiment, discriminatory ability of an exemplary colorimetric sensor may be set at a highest value by using an optimum amount or an optimum concentration of each chemical receptor of an exemplary array of chemical receptors. Furthermore, discriminatory ability of an exemplary colorimetric sensor may be set at an exemplary highest value by using an optimum pre-determined time period of interaction between an exemplary saliva sample and an array of chemical receptors. In an exemplary embodiment, a high discriminatory ability of an exemplary colorimetric sensor may lead to a high accurate discriminating patients from healthy individuals. In an exemplary embodiment, a high discriminatory ability of an exemplary colorimetric sensor may include an accurate classification between exemplary saliva samples associated with COVID-19 infected patients and exemplary saliva samples associated with healthy individuals. In an exemplary embodiment, an optimum amount or an optimum concentration of each chemical receptor and an optimum time period of interaction between an exemplary saliva sample and an array of chemical receptors may be obtained using a discrimination ability function (DAF) analysis. In an exemplary embodiment, a discrimination ability function (DAF) analysis may include applying an exemplary method 300 to a set of saliva samples acquired from two groups of people with known status of COVID-19 infection. In an exemplary embodiment, exemplary two groups of people may include a first group of COVID-19 infected patients and a second group of healthy individuals. In an exemplary embodiment, a DAF value may be calculated for a plurality of tests that may be done according to exemplary method 300. In an exemplary embodiment, an exemplary plurality of tests may include a first plurality of tests with a respective set of different amounts or concentrations of each chemical receptor. In an exemplary embodiment, the plurality of tests may further include a second plurality of tests with a respective set of different time periods of interaction between an exemplary saliva sample and an exemplary array of chemical receptors. In an exemplary embodiment, an exemplary DAF factor may be calculated using a relation defined by Equation 10:

$$DAF = \frac{2\sum_m \left(\overline{|\Delta V|}_m - \overline{|\Delta V|}\right)^2}{\sum_m \sum_k \left(|\Delta V|_{mk} - \overline{|\Delta V|}_m\right)^2}, \quad \text{Equation 10}$$

Where, $|\Delta V|_{mk}$ is magnitude of an exemplary difference color value vector associated with $k^{th}$ saliva sample in group m that may be calculated using Equation 8 described herein above, m is 1 for exemplary first group of COVID-19 infected patients and m is 2 for exemplary second group of healthy individuals, $\overline{|\Delta V|}_m$ is an average of total magnitudes of exemplary difference color value vectors of exemplary respective saliva samples in group m, and $\overline{\Delta V}$ is an average magnitude of exemplary difference color value vectors for all the plurality of tests. In an exemplary embodiment, a highest discriminatory ability may be obtained at a highest calculated DAF value.

Figure 5:
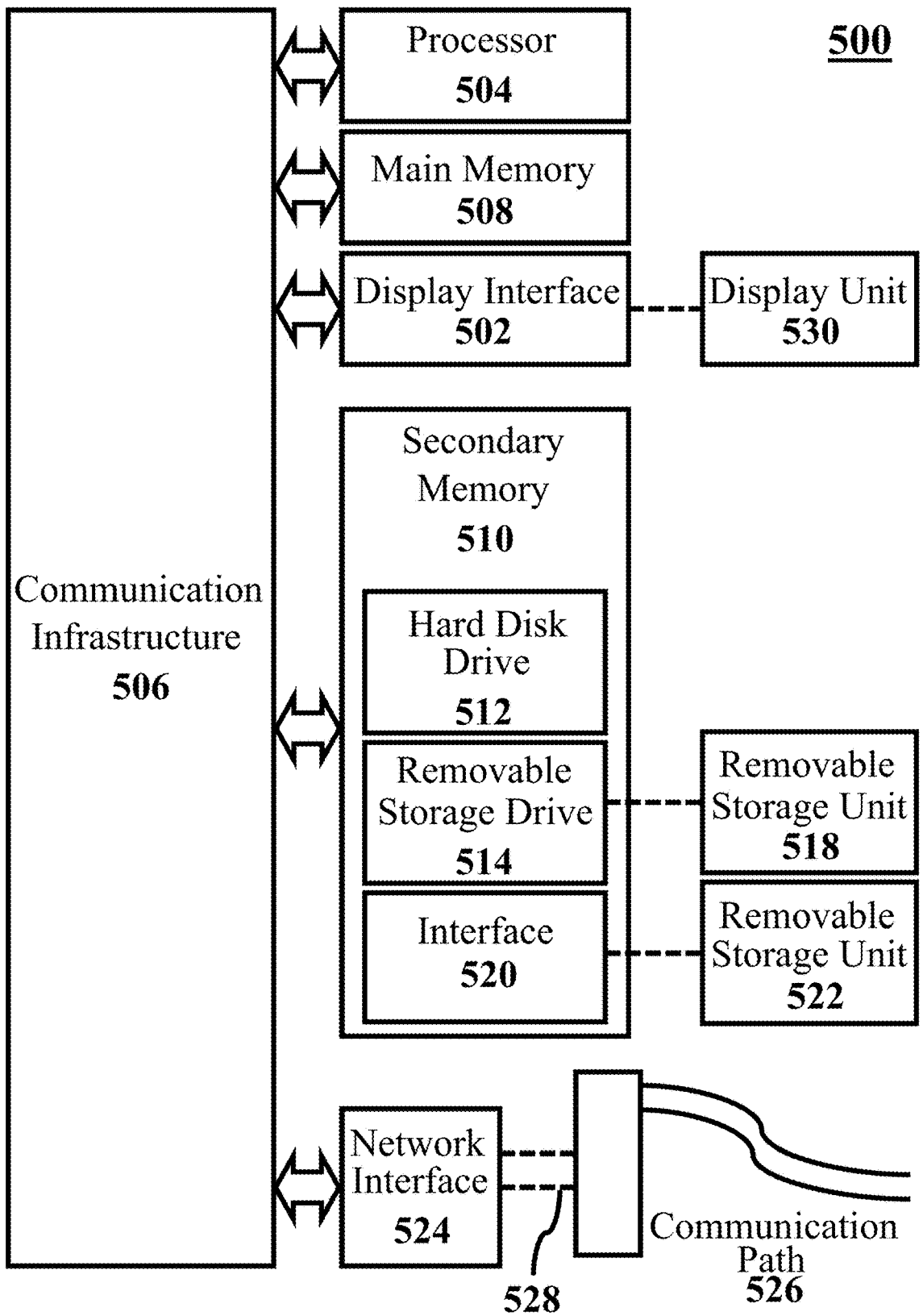
FIG. 5 shows an example computer system in which an embodiment of the present disclosure, or portions thereof, may be implemented as computer-readable code, consistent with one or more exemplary embodiments of the present disclosure.

In an exemplary embodiment, one or more steps of methods 300 and 400 and also DAF analysis may be performed by processing unit 202. FIG. 5 shows an example computer system 500 in which an embodiment of the present disclosure, or portions thereof, may be implemented as computer-readable code, consistent with one or more exemplary embodiments of the present disclosure. For example, computer system 500 may include an example of processing unit 202 illustrated in FIG. 2, one or more steps of exemplary methods 300, and 400 presented in FIGS. 3 and 4, and exemplary DAF analysis may be implemented in computer system 500 using hardware, software, firmware, tangible computer readable media having instructions stored thereon, or a combination thereof and may be implemented in one or more computer systems or other processing systems. Hardware, software, or any combination of such may embody any of the modules and components in FIG. 2.

If programmable logic is used, such logic may execute on a commercially available processing platform or a special purpose device. One ordinary skill in the art may appreciate that an embodiment of the disclosed subject matter can be practiced with various computer system configurations, including multi-core multiprocessor systems, minicomputers, mainframe computers, computers linked or clustered with distributed functions, as well as pervasive or miniature computers that may be embedded into virtually any device.

For instance, a computing device having at least one processor device and a memory may be used to implement the above-described embodiments. A processor device may be a single processor, a plurality of processors, or combinations thereof. Processor devices may have one or more processor "cores".

An embodiment of the present disclosure is described in terms of this example computer system 500. After reading this description, it will become apparent to a person skilled in the relevant art how to implement the invention using other computer systems and/or computer architectures. Although operations may be described as a sequential process, some of the operations may in fact be performed in parallel, concurrently, and/or in a distributed environment, and with program code stored locally or remotely for access by single or multi-processor machines. In addition, in some embodiments the order of operations may be rearranged without departing from the spirit of the disclosed subject matter.

Processor device 504 may be a special purpose or a general-purpose processor device. As will be appreciated by persons skilled in the relevant art, processor device 504 may also be a single processor in a multi-core/multiprocessor system, such system operating alone, or in a cluster of computing devices operating in a cluster or server farm. Processor device 504 may be connected to a communication infrastructure 506, for example, a bus, message queue, network, or multi-core message-passing scheme.

In an exemplary embodiment, computer system 500 may include a display interface 502, for example a video connector, to transfer data to a display unit 530, for example, a monitor. Computer system 500 may also include a main memory 508, for example, random access memory (RAM), and may also include a secondary memory 510. Secondary memory 510 may include, for example, a hard disk drive 512, and a removable storage drive 514. Removable storage drive 514 may include a floppy disk drive, a magnetic tape drive, an optical disk drive, a flash memory, or the like. Removable storage drive 514 may read from and/or write to a removable storage unit 518 in a well-known manner. Removable storage unit 518 may include a floppy disk, a magnetic tape, an optical disk, etc., which may be read by and written to by removable storage drive 514. As will be appreciated by persons skilled in the relevant art, removable storage unit 518 may include a computer usable storage medium having stored therein computer software and/or data.

In alternative embodiments, secondary memory 510 may include other similar means for allowing computer programs or other instructions to be loaded into computer system 500. Such means may include, for example, a removable storage unit 522 and an interface 520. Examples of such means may include a program cartridge and cartridge interface (such as that found in video game devices), a removable memory chip (such as an EPROM, or PROM) and associated socket, and other removable storage units 522 and interfaces 520 which allow software and data to be transferred from removable storage unit 522 to computer system 500.

Computer system 500 may also include a communications interface 524. Communications interface 524 allows software and data to be transferred between computer system 500 and external devices. Communications interface 524 may include a modem, a network interface (such as an Ethernet card), a communications port, a PCMCIA slot and card, or the like. Software and data transferred via communications interface 524 may be in the form of signals, which may be electronic, electromagnetic, optical, or other signals capable of being received by communications interface 524. These signals may be provided to communications interface 524 via a communications path 526. Communications path 526 carries signals and may be implemented using wire or cable, fiber optics, a phone line, a cellular phone link, an RF link or other communications channels.

In this document, the terms "computer program medium" and "computer usable medium" are used to generally refer to media such as removable storage unit 518, removable storage unit 522, and a hard disk installed in hard disk drive 512. Computer program medium and computer usable medium may also refer to memories, such as main memory 508 and secondary memory 510, which may be memory semiconductors (e.g. DRAMs, etc.).

Computer programs (also called computer control logic) are stored in main memory 508 and/or secondary memory 510. Computer programs may also be received via communications interface 524. Such computer programs, when executed, enable computer system 500 to implement different embodiments of the present disclosure as discussed herein. In particular, the computer programs, when executed, enable processor device 504 to implement the processes of the present disclosure, such as the operations in exemplary methods 300 and 400 illustrated by FIGS. 3 and 4, discussed above. Accordingly, such computer programs represent controllers of computer system 500. Where an exemplary embodiment of methods 300 and 400 is implemented using software, the software may be stored in a computer program product and loaded into computer system 500 using removable storage drive 514, interface 520, and hard disk drive 512, or communications interface 524.

Embodiments of the present disclosure also may be directed to computer program products including software stored on any computer useable medium. Such software, when executed in one or more data processing device, causes a data processing device to operate as described herein. An embodiment of the present disclosure may employ any computer useable or readable medium. Examples of computer useable mediums include, but are not limited to, primary storage devices (e.g., any type of random access memory), secondary storage devices (e.g., hard

EXAMPLE 1: FABRICATION OF A COLORIMETRIC SENSOR

In this example, a colorimetric sensor similar to colorimetric sensors 100 and 212, described herein above, was fabricated. To design the colorimetric sensor with an origami structure, a rectangular pattern with dimensions of 1.5 cm×1 cm was drawn using a processing unit similar to processing unit 202. The pattern consisted of injection (a white rectangle) and detection (12 small circles) parts. The designed pattern was printed on a filter paper substrate using a printer device. Black regions became hydrophobic by heating the filter paper at 200° C. for 45 min. The small circles were filled with relevant chemical receptors. About 0.12 µL of a solution containing each chemical receptor was dropped on each respective small circle using a micropipette. An array of 12 chemical receptors, including BSA-AuNPs, CA-AuNPs, PGA-AuNPs, Bromophenol red+DWES, Bromocresol purple+DWES, Bromocresol purple+PBA, Fe(III)TPPCL, Mn(III)T(4-OH)PP(OAc), Sn(II)TPP, V(IV)-Py, Fe(II)-Py, Cu(II)-Py were prepared and deposited on a respective array of 12 individual circular areas on a detection zone of the colorimetric sensor. For preparation of pH-sensitive organic dyes, Lewis donor/acceptor chemical receptors, and metal ion complexes, solutions of dyes and porphyrins were prepared in ethanol (EtOH) except pyrocatechol violet (Py) that dissolved in deionized water. To provide DWES solution, a container was poured by 2, 4-dinitrophenylhydrazine (0.4 g), EtOH (10.0 mL), deionized water (3.0 mL), and $H_2SO_4$ (2.0 mL) and the poured materials were stirred for 10 min. Then, a prepared mixture was filtered and an obtained solution was used for chemical receptors including DWES. Dye-based receptors were formed by mixing bromophenol red and bromocresol purple dye solutions and an additive such as DWES or phenylboronic acid (PBA) in ethanol with a concentration of an additive of 2.0 mol $L^{-1}$ in an obtained solution. Dye concentration and volume ratio of mixture components were optimized at a ratio of organic dye:additive equal to 3:1 using a discrimination ability function (DAF) analysis as described herein below in optimization of sensing agents. Porphyrin-based dyes including [meso-tetraphenylporphyrin]Iron(III) chloride (Fe(III)TPPCl), [meso-tetraphenylporphyrin]-Tin (II) (Sn(II)TPP) and meso-tetrakis(4-hydroxyphenyl) porphyrin-manganese (III) acetate (Mn(III)T(4-OH)PP(OAc)) were obtained and a solution with an optimal concentration of 4.5 mg $mL^{-1}$ (obtained in a DAF-based optimization process describe herein below) of each dye compound was used as sensing element without any modifications. Moreover, nanoparticle-based receptors were provided by synthesis of gold nanoparticles (AuNPs) coated by capping agents consisting of Bovine serum albumin (BSA), caffeic acid (CA), and poly glutamic acid (PGA). For preparing BSA-AuNPs, a boiling solution of $HAuCl_4$ (100.0 mL, 0.001 mol $L^{-1}$) and an aqueous solution of sodium citrate (1.0 mL, 1% V/W) were mixed together to form AuNPs. The mixture was cooled on a stirrer for 15 min. Subsequently, a BSA solution (3.0 mL, 20.0 mg $mL^{-1}$) was added and the obtained solution was kept under stirring condition for 20 hours. Then, unreacted coating agent was separated by centrifuging the mixture at 10000 rpm for 15 min. For preparing CA-AuNPs, a solution containing $HAuCl_4$ (60.0 µl, 0.01 mol $L^{-1}$), CA (280.0 µl, 0.005 mol $L^{-1}$), and deionized water (3.660 mL) was kept under reflux and stirring condition at 50° C. for 4 hours. Additionally, PGA-AuNPs were prepared by adding PGA solution (1.0 mL, 0.1% W/V) to a round bottom flask filled by $HAucl_4$ (20.0 mL, 0.05 mol $L^{-1}$) and D-glucose (10.0 mL, 0.03 mol $L^{-1}$) solutions to form a mixture. The mixture was alkalized by adding sodium hydroxide (NaOH) solution (280.0 µL, 0.5 mol $L^{-1}$). Each prepared AuNPs solution was subjected to a freeze-dryer and the result powder was crushed fine in a mortar. To prepare AuNPs-containing solution for filling into respective circular areas of the colorimetric sensor, the obtained powders were re-dispersed in deionized water. As described herein below in optimization of sensing agents, prepared AuNPs solutions were used with a concentration of 4.5 mg $mL^{-1}$ in each respective circular area. Additionally, to prepare metal ion complexes, three mixtures of Py (50.0 µL) and a metal ion solution including V (IV), Fe (II) and Cu (II) was added to 100.0 µL of 0.1 mol $L^{-1}$ borate buffer (pH=9.0). Metal ion solutions were prepared using vanadyl sulfate pentahydrate ($VOSO_4.5H_2O$), iron(II) chloride tetrahydrate ($Fecl_2.4H_2O$), and copper(II) nitrate trihydrate ($Cu(NO_3)_2.3H_2O$). The same volumes and concentrations of dye and metal ion were used to prepare this mixture. As described herein below in an optimized state of sensing agents, prepared metal ion complex solutions were used with a concentration of 0.05 mol $L^{-1}$ in each respective circular area.

Figure 6A:
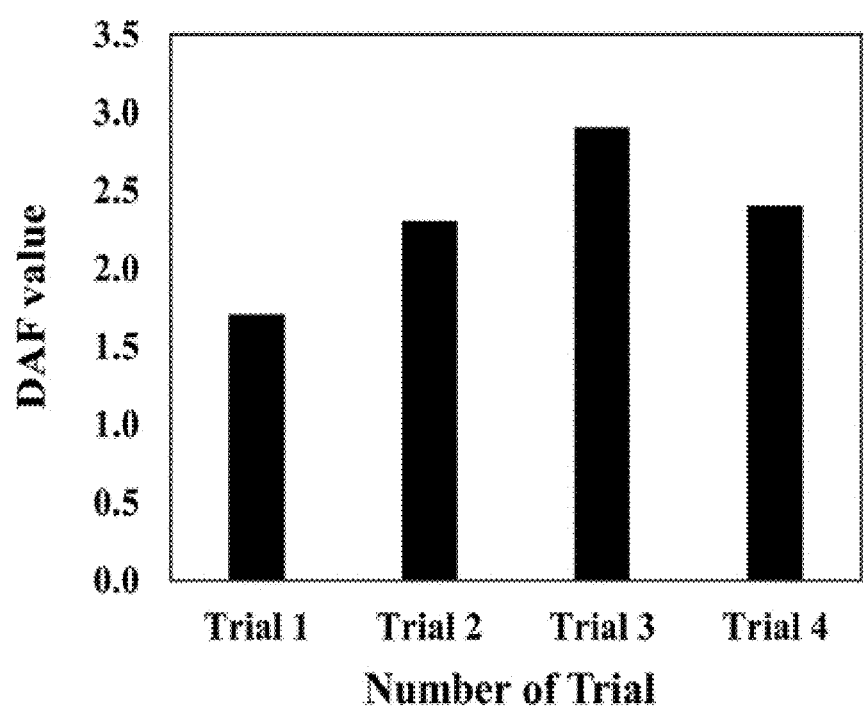
FIG. 6A shows a chart with discrimination ability function (DAF) factor analysis results for optimizing concentration of each exemplary chemical receptor, consistent with one or more exemplary embodiments of the present disclosure.
Figure 6B:
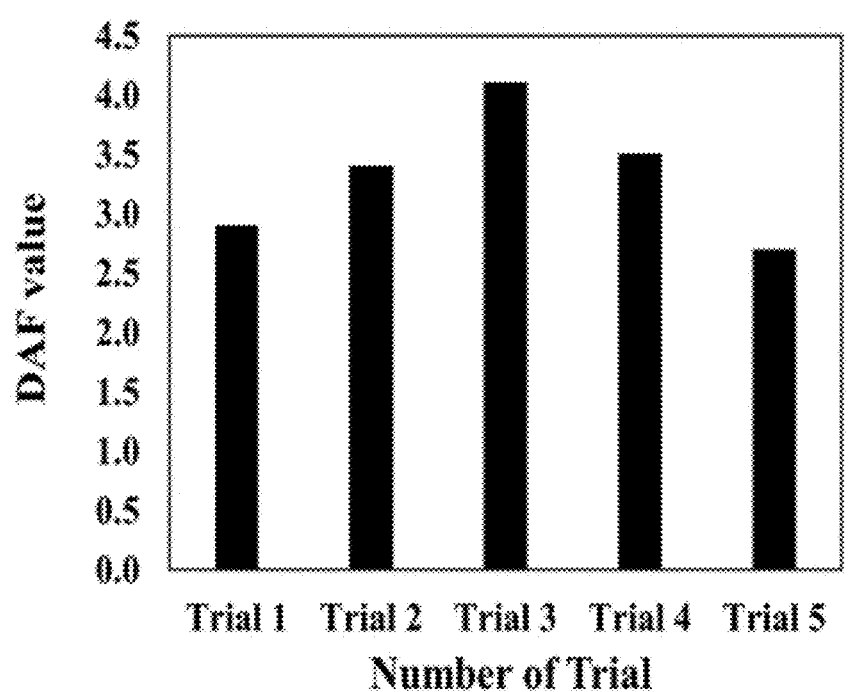
FIG. 6B shows a chart with DAF factor analysis results for different types of solutions containing organic dyes and additives, consistent with one or more exemplary embodiments of the present disclosure.
Figure 6C:
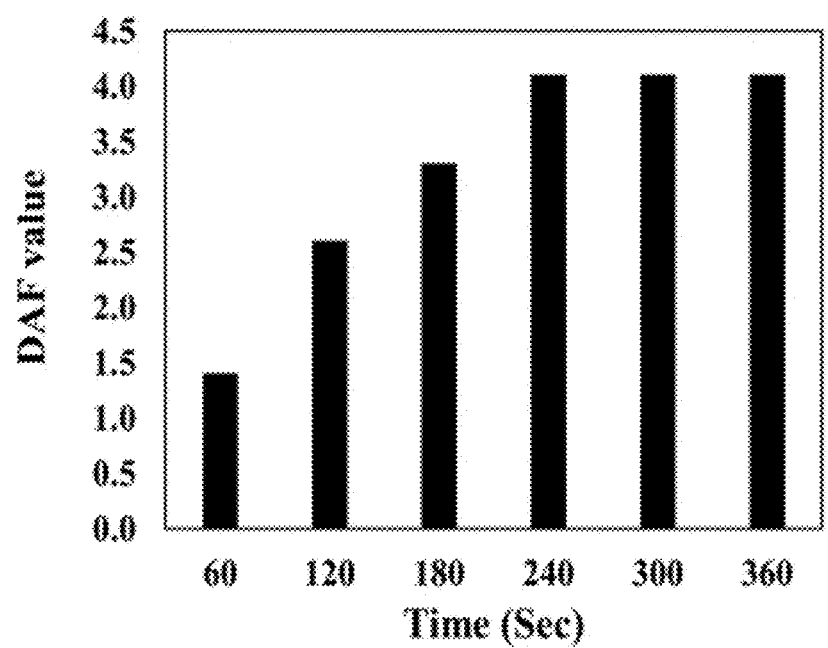
FIG. 6C shows a chart with DAF factor analysis results for a range of period of time between 0 to 360 seconds of incubation of an exemplary saliva sample and an exemplary array of chemical receptors, consistent with one or more exemplary embodiments of the present disclosure.

Furthermore, an optimization process was done to achieve optimum amount/concentration of each chemical receptor and optimum time period of interaction between an exemplary saliva sample and the array of chemical receptors; thereby, leading to the highest accuracy classification of the fabricated colorimetric sensor to discriminate patients from healthy individuals. In this regard, a plurality of tests similar to exemplary method 300 were performed on 10 saliva secretions samples acquired from 5 infected and 5 healthy individuals. Each sample was undergone for three times in these tests. For each sample, is magnitude of an exemplary difference color value vector (|ΔV|) of an exemplary array of chemical receptors was used to calculate ratio of within-group variations and between-group variations according to a discrimination ability function (DAF) factor analysis. FIG. 6A shows a chart 600 with discrimination ability function (DAF) factor analysis results using trials described in Table 1 for optimizing concentration of each exemplary chemical receptor, consistent with one or more exemplary embodiments of the present disclosure. FIG. 6B shows a chart 602 with DAF factor analysis results for different types of solutions containing organic dyes and additives using trials described in Table 2, consistent with one or more exemplary embodiments of the present disclosure. FIG. 6C shows a chart 604 with DAF factor analysis results for a range of period of time between 0 to 360 seconds of incubation of an exemplary saliva sample and an exemplary array of chemical receptors, consistent with one or more exemplary embodiments of the present disclosure.

TABLE 1

Tests for optimization of concentration of each chemical receptor

| Number of trial | Information |
| --- | --- |
| Trial 1 | NPs (1.5 mg $mL^{-1}$), Organic dyes* (0.5 mg $mL^{-1}$), Porphyrins (1.5 mg $mL^{-1}$), Metal complexes** (0.005 mol $L^{-1}$) |
| Trial 2 | NPs (3.0 mg $mL^{-1}$), Organic dyes (1.5 mg $mL^{-1}$), Porphyrins (3.0 mg $mL^{-1}$), Metal complexes** (0.01 mol $L^{-1}$) |

TABLE 1-continued

Tests for optimization of concentration of each chemical receptor

| Number of trial | Information |
|---|---|
| Trial 3 | NPs (4.5 mg mL$^{-1}$), Organic dyes (2.5 mg mL$^{-1}$), Porphyrins (4.5 mg mL$^{-1}$), Metal complexes** (0.05 mol L$^{-1}$) |
| Trial 4 | NPs (6.0 mg mL$^{-1}$), Organic dyes (3.5 mg mL$^{-1}$), Porphyrins (6.0 mg mL$^{-1}$), Metal complexes** (0.10 mol L$^{-1}$) |

*Mixing organic dyes with additives with ratio of 1:1 V/V
**Dissolving metal complexes in borate buffer (0.1 mol L$^{-1}$)

TABLE 2

Tests for optimization of volume ratio of an organic dye to an additive in a solution containing the organic dye and additive

| Number of trial | The volume ratio of (reagent*:additive**) |
|---|---|
| Trial 1 | 1:1 |
| Trial 2 | 2:1 |
| Trial 3 | 3:1 |
| Trial 4 | 4:1 |
| Trial 5 | 5:1 |

*Reagents are organic dyes
**Additives are DWES and PBA

As inferred from FIG. 6A, sensor response may be changed by varying sensing component concentrations. Undesirable results may be obtained for lower concentrations due to a reduction in sufficient reactive sites for capturing saliva species. On the other hand, at higher concentrations, masking of color changes arisen from interactions leads to undesirable results so that color intensity of chemical receptors is high at higher concentrations and reduces color changes due to interactions of chemical receptors with metabolites of saliva. Referring to FIG. 6A, the third trial among the designed trails (Table 1) may provide a suitable concentration for fabrication of an exemplary array of chemical receptors. Organic dyes may be mixed with additives in order to identify a specific class of markers. An amount of additives needs to be adjusted at an appropriate value, thus allowing for a complete interaction with saliva chemical compositions, while also preventing active sites of receptors from blockage. Five different trials were designed as described in Table 2, and the highest DAF value was obtained for a mixture with a volume ratio of receptor:additive (3:1) referring to FIG. 6B. Moreover, responses of an exemplary fabricated colorimetric sensor for infected and healthy samples were compared with each other for a specific period of time of incubating a saliva sample on an exemplary sensor. The results observed in FIG. 6C, illustrate that changes in color of chemical receptors become fixed after about 4 minutes of saliva sample injection; indicating an equilibrium between chemical markers in saliva samples and sensor components. This time period was selected to collect colorimetric data of the subsequent tests.

EXAMPLE 2: COVID-19 INFECTION DIAGNOSIS USING A COLORIMETRIC SENSOR

In this example, color changes of an exemplary array of chemical receptors fan exemplary colorimetric sensor fabricated according to EXAMPLE 1 herein above was monitored and analyzed utilizing a method similar to exemplary method 300 to diagnose COVID-19 patients and differentiate them from healthy individuals. 115 participants were with an age range of 21-80 years were divided into three groups, including patients (60 samples), healthy individuals (55 samples), and cured people after an infection with COVID-19 virus (15 samples). Demographic data of the participants is shown in Table 3. The patients were examined by a pulmonologist and their disease was confirmed using chest imaging and real-time reverse-transcriptase polymerase-chain-reaction (rRT-PCR) results. The patients who had taken medication were excluded from tests. After two months, patients undergoing a treatment process (cured samples) were recalled for a new investigation. The participants were asked to rinse their mouths twice with water to remove physical particles from their saliva samples. After 15 min, 500.0 µL of saliva of each person was collected in a sterile Falcon tube, and stored in an ice pack before test. Oral impurities were removed by centrifugation of saliva sample at 10,000 rpm and 4° C. for 10 min. For conducting tests, injection and detection parts of a colorimetric sensor (similar to colorimetric sensors 100 and 212) were connected to each other by folding exemplary colorimetric sensor. To provide an appropriate alignment, the folded colorimetric sensor was placed between two planar holders. The colorimetric sensor was exposed to 40.0 µL of a clear supernatant saliva sample. Chemical markers in saliva simultaneously interacted with all sensing components of the colorimetric sensor. Efficient interactions caused chemical receptors to change their color.

TABLE 3

Demographic data of the studied population

| Variable | Patient with Covid-19 | Healthy controls |
|---|---|---|
| Studied samples | 60 | 55 |
| Age | | |
| (Mean ± SD) | 52.15 ± 14.01 | 48.10 ± 11.15 |
| O$_2$ saturation*** | 91.29 (75-97) | 97.45 (96-99) |
| RT-PCR* | Positive (91.6%) | Negative (100%) |
| N gene | 24.30 (15-32) | |
| RdRp gene*** | 24.35 (15-34) | |
| Smoke | 5 | 15 |
| Comorbidities | | |
| Cardiovascular disease | 6 | 8 |
| Chronic kidney disease | 7 | 8 |
| Asthma | 1 | 1 |
| Diabetes | 11 | 9 |
| COPD** | 4 | 3 |
| Chronic liver disorder | 1 | 5 |
| Hypertension | 11 | 9 |
| Symptoms | | |
| Cough | 56 | |
| Dyspnea | 48 | |
| Headache | 53 | |
| Fever | 49 | |
| Myalgia | 43 | |
| Nausea and Diarrhea | 24 | |
| Anorexia | 38 | |
| Sneezing | 8 | |

*RT-PCR: Reverse transcription polymerase chain reaction
**COPD: Chronic obstructive pulmonary disease
***Data are represented as median and interquartile range.

Analysis of color changes of chemical receptors showed that among nanoparticles-based receptors, color of CA-AuNPs changes in the presence of healthy saliva samples. Alternatively, other NPs have no tendency to interact with metabolites of both healthy and infected saliva secretions.

Metabolites of infected samples change color of two organic dyes mixed with DWES. Responses of porphyrins to different tested groups strongly depend on central metal ion and constituents of porphyrin cage. An infected sample illuminates a sensing component containing Fe(III)TPPCl, whereas healthy saliva species interact with Mn(III)T(4-OH)PP(OAc). V(IV)-Py complex participates in indicator displacement reaction with chemical markers of healthy samples. All tested groups may affect color of Fe(II)-Py and Cu(II)-Py complexes. Furthermore, no responses are recorded from Sn(II)TPP and mixture of bromocresol purple with PBA. During treatment process, composition of saliva of cured samples shifted from patient to healthy profiles. Detection process was repeated for cured people after a month. Markers of saliva samples of cured people altered color of Fe(III)TPPCl (as a specific receptor of infected samples) and V(IV)-Py (from sensory elements responding to healthy samples). The results explained that saliva metabolite profiles of cured people are different from compounds of healthy samples due to body disorders caused by viral infections.

Figure 7A:
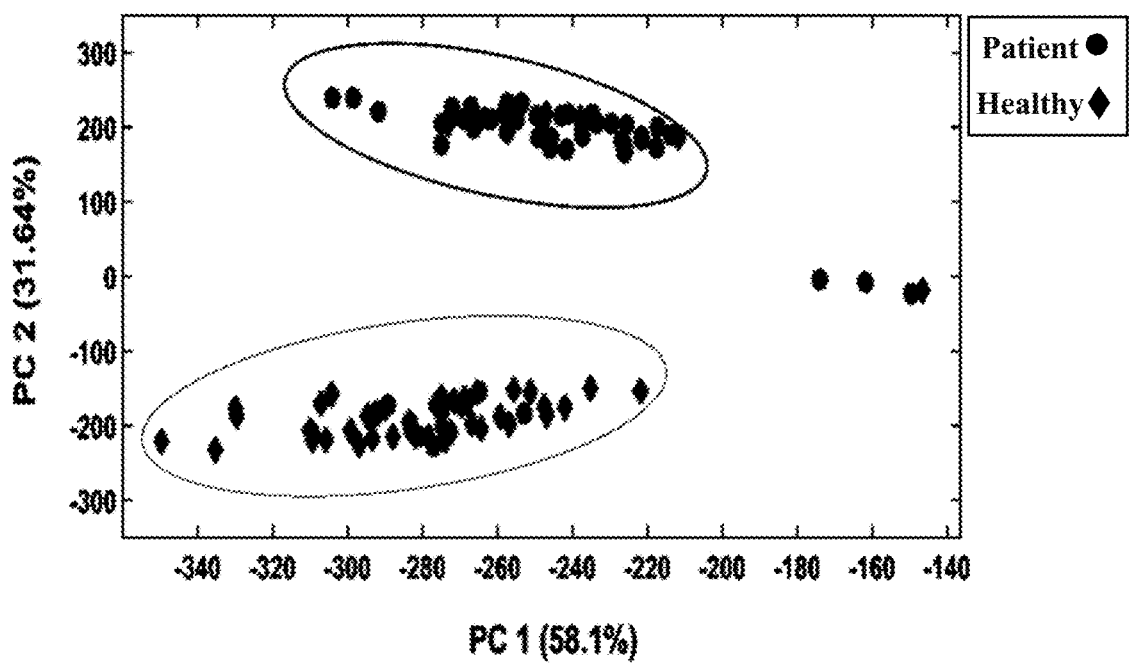
FIG. 7A shows a chart with score plots obtained by principle component analysis-linear discriminate analysis (PCA-DA) analysis for classification of patients and healthy controls using an exemplary fabricated colorimetric sensor with optimized array of chemical receptors compositions after 4 min incubation of an exemplary array of chemical receptors and saliva samples, consistent with one or more exemplary embodiments of the present disclosure.
Figure 7B:
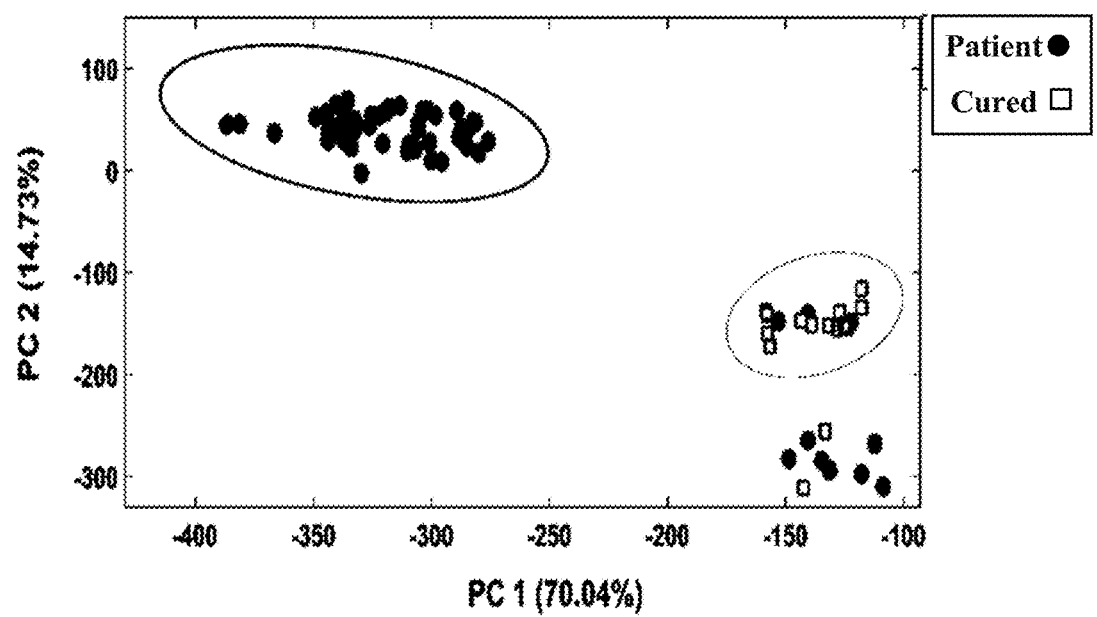
FIG. 7B shows a chart with score plots obtained by PCA-DA analysis for classification of patients and cured individuals using an exemplary fabricated colorimetric sensor with optimized array of chemical receptors compositions after 4 min incubation of an exemplary array of chemical receptors and saliva samples, consistent with one or more exemplary embodiments of the present disclosure.
Figure 7C:
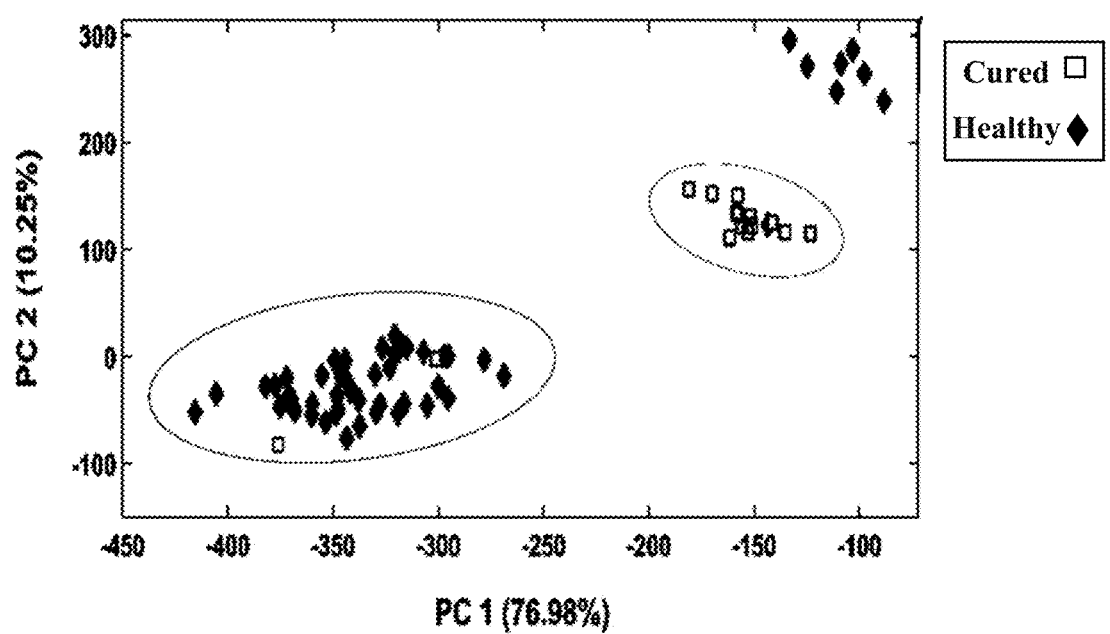
FIG. 7C shows a chart with score plots obtained by PCA-DA analysis for classification of healthy controls and cured individuals using an exemplary fabricated colorimetric sensor with optimized array of chemical receptors compositions after 4 min incubation of an exemplary array of chemical receptors and saliva samples, consistent with one or more exemplary embodiments of the present disclosure.

In this respect, a scanner device was used to monitor chemical receptors discoloration. Color of receptors were evaluated using a processing unit similar to processing unit 202. Color numerical values corresponding to red, green and blue color components were calculated for each chemical receptor. Since array of chemical receptors had 12 components, a vector containing 36 elements was generated for each test. Evaluation of discrimination ability of exemplary colorimetric sensor was performed by principle component analysis-linear discriminate analysis (PCA-DA). Image analysis data were aligned in three individual matrices and color difference data were collected in matrices with sizes of (115×36), (75×36), and (70×36) for patient-healthy, patient-cured, and healthy-cured classes, respectively. These data were inserted into PCA-DA algorithm for cluster statistical analysis. FIGS. 7A-7C show respective charts 700, 702, and 704 with score plots obtained by PCA-DA analysis for classification of patients, healthy controls and cured participants using an exemplary fabricated colorimetric sensor with optimized array of chemical receptors compositions after 4 min incubation of an exemplary array of chemical receptors and saliva samples, consistent with one or more exemplary embodiments of the present disclosure. FIG. 7A shows a chart 700 with score plots for classification of patients and healthy controls, FIG. 7B shows a chart 702 with score plots for classification of patients and cured individuals, and FIG. 7C shows a chart 704 with score plots for classification of healthy controls and cured individuals. The score plots depicted in FIGS. 7A-7C show that over 84% of total data variances are distributed in space of two first principal components of PCA-DA analysis. Shown diagrams indicate a good distinction between two classes of each matrix so that 50 patients, 47 healthy individuals, and 13 cured samples can be classified in their corresponding classes with sensitivities of 83.3%, 85.4%, and 86.6%, respectively. In detail, COVID-19 patients (60 samples) and healthy individuals (55 samples) were discriminated with 84.3% accuracy. Moreover, results showed that saliva composition of cured and healthy participants is different from each other with accuracy of 85.7%.

EXAMPLE 3: DIAGNOSIS OF COMORBIDITIES ALONG WITH COVID-19 INFECTION

In this example, potential of an exemplary colorimetric sensor, system and method for screening people with cardiovascular, chronic kidney, asthma, diabetes, chronic obstructive pulmonary, chronic liver and hypertension diseases was investigated utilizing exemplary colorimetric sensor, system, and method of EXAMPLE 2. Saliva samples of participants may contain chemical markers associated with other diseases more than COVID-19 infection as represented in Table 3. For each disease, specific chemicals may appear in saliva secretions. As an example, a person with kidney disease may be diagnosed by monitoring amounts of urea, creatinine, and uric acid. Concentration of compounds such as glucose, 1,3-dihydroxyacetone, lactate, citrulline, ornithine, leucine, and ethanolamine varies in saliva composition of diabetic and healthy subjects. Difference between smokers and non-smokers may be achieved by determining amounts of some species such as thiocyanate, ionizable iodine, OH-cotinine, tyramine and cadaverine. By delving into exemplary colorimetric sensor results, it was found that chemical composition of saliva samples obtained from individuals with kidney disease leads to aggregation of BSA-AuNPs, while also changing NPs color from red to purple. Furthermore, bromocresol purple combined with PBA turns blue in the presence of salivary metabolites of diabetic patients. Response of Sn(II)TPP receptor is only visible for smokers' samples. Number of people being properly clustered is also listed in Table 3. Based on saliva marker analysis, performance of exemplary colorimetric sensor for detection of smokers, people with diabetes, and people with kidney disease are calculated to be 70%, and 65% and 66.6%, respectively.

EXAMPLE 4: DETECTING SEVERITY OF COVID-19 INFECTION

Figure 8:
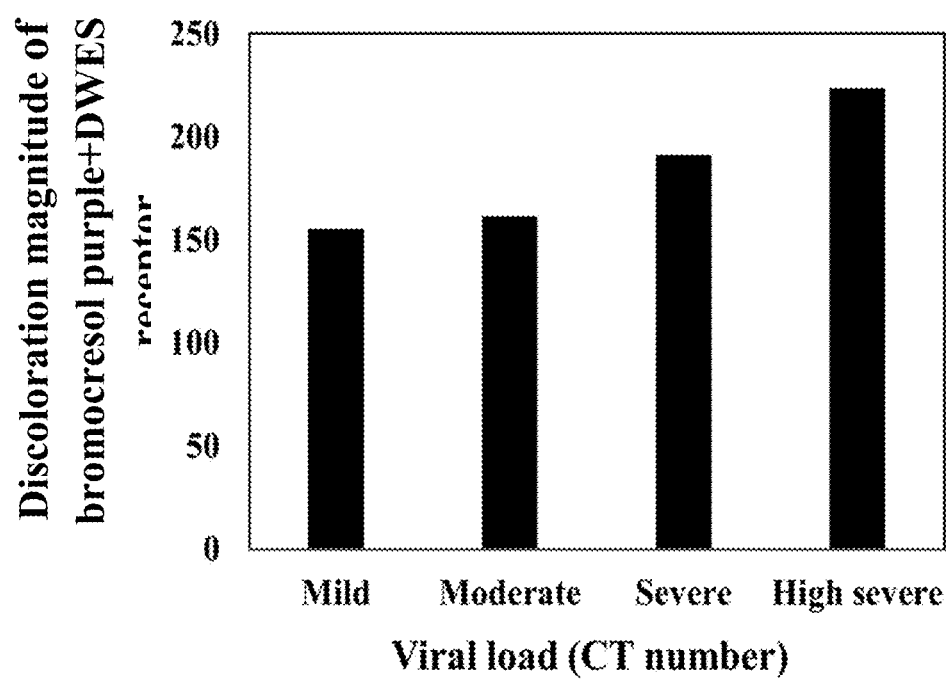
FIG. 8 shows a chart with magnitude of an exemplary difference color value vector for chemical receptor bromocresol purple combined with DWES (bromocresol purple+DWES) increases by rising a severity of COVID-19 infection, consistent with one or more exemplary embodiments of the present disclosure.

In this example, a colorimetric sensor similar to colorimetric sensors 100 and 212 and a system similar to exemplary system 200 was utilized through conducting a method similar to exemplary method 300 for detecting severity of COVID-19 infection by estimating viral load of COVID-19 virus associated with a rRT-PCR analysis in a COVID-19 infected patient. A viral load value (based on N gene cycle threshold (CT) value) obtained from a rRT-PCR analysis is a criterion for determining COVID-19 infection severity. COVID-19 patients may be divided into 4 groups with low, moderate, high and very high infection severity. Viral loads may be distributed in numerical ranges of (28-32) for low, (23-27) for moderate, (18-22) for severe, and (15-17) for high severe classes. In this example, discoloration of an exemplary array of chemical receptors (or only one specific receptor) for each saliva sample was compared with a respective viral load value. FIG. 8 shows a chart 800 with magnitude of an exemplary difference color value vector for chemical receptor bromocresol purple combined with DWES (bromocresol purple+DWES) increases by rising a severity of COVID-19 infection, consistent with one or more exemplary embodiments of the present disclosure. A positive and pronounced linear relationship between color changes of bromocresol purple+DWES receptor and virus load value with a Pearson correlation coefficient of 0.898 (P-value<0.001) may be obtained. Visual analysis of bromocresol purple+DWES receptor showed that color of bromocresol purple+DWES receptor changes from orange to light brown for mild infection and dark brown for high severe infection. A physician may use monitoring and quantifying discoloration of bromocresol purple+DWES receptor to determine a severity of COVID-19 infection disease and subsequently a range of viral load.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments. This is for purposes of streamlining the disclosure, and is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separately claimed subject matter.

While various embodiments have been described, the description is intended to be exemplary, rather than limiting and it will be apparent to those of ordinary skill in the art that many more embodiments and embodiments are possible that are within the scope of the embodiments. Although many possible combinations of features are shown in the accompanying figures and discussed in this detailed description, many other combinations of the disclosed features are possible. Any feature of any embodiment may be used in combination with or substituted for any other feature or element in any other embodiment unless specifically restricted. Therefore, it will be understood that any of the features shown and/or discussed in the present disclosure may be implemented together in any suitable combination. Accordingly, the embodiments are not to be restricted except in light of the attached claims and their equivalents. Also, various modifications and changes may be made within the scope of the attached claims.

What is claimed is:

1. A system for detecting COVID-19 infection, comprising:
   a colorimetric sensor, comprising:
     a detection zone, comprising an array of chemical receptors deposited on a respective array of individual areas of a hydrophilic paper, the array of chemical receptors configured to interact with a saliva sample acquired from a person suspected to be infected by COVID-19 virus, the array of chemical receptors comprising:
       a first array of three chemical receptors comprising three respective aqueous solutions of three distinctive functionalized gold nanoparticles (AuNPs), each aqueous solution with a concentration of 4.5 mg mL$^{-1}$ of respective functionalized AuNPs, the three distinctive functionalized AuNPs comprising:
         AuNPs functionalized with bovine serum albumin;
         AuNPs functionalized with caffeic acid; and
         AuNPs functionalized with poly glutamic acid;
       a second array of three chemical receptors comprising three distinctive mixtures of an organic dye and an additive, each mixture with a volume ratio of organic dye:additive equal to 3:1, the three distinctive mixtures comprising:
         a mixture of bromophenol red and DWES;
         a mixture of bromocresol purple and DWES; and
         a mixture of bromophenol red and phenylboronic acid,
         wherein the DWES is a mixture of 2,4-dinitrophenylhydrazine, deionized water, Ethanol (EtOH), and $H_2SO_4$;
       a third array of three chemical receptors comprising three respective solutions of 4.5 mg mL$^{-1}$ of three distinctive porphyrin-based dyes in ethanol, the three distinctive porphyrin-based dyes comprising:
         [meso-tetraphenylporphyrin]Iron(III) chloride (Fe(III)TPPCl);
         meso-tetrakis(4-hydroxyphenyl) porphyrin-manganese (III) acetate (Mn(III)T(4-OH)PP(OAc)); and
         [meso-tetraphenylporphyrin]-Tin (II) (Sn(II)TPP); and
       a fourth array of three chemical receptors comprising three respective solutions of 0.05 mol L$^{-1}$ of three distinctive metal ion complexes in a borate buffer solution with pH value of 9.0, the three distinctive metal ion complexes comprising:
a complex of pyrocatechol violet (Py) with V (IV) ions;
a complex of Py with Fe (II) ions; and
a complex of Py with Cu (II) ions; and
an injection zone configured to inject the saliva sample thereon, the injection zone comprising a bare part of the hydrophilic paper covering the array of chemical receptors, the hydrophilic paper folded along a line between the injection zone and detection zone, the injection zone covering the array of chemical receptors configured to allow the injected saliva sample to penetrate from the injection zone to the array of chemical receptors;
an image-capturing device, configured to capture an image of the detection zone; and
a processing unit electrically connected to the image-capturing device, the processing unit comprising:
a memory having processor-readable instructions stored therein; and
a processor configured to access the memory and execute the processor-readable instructions, which, when executed by the processor configures the processor to perform a method, the method comprising:
capturing, utilizing the image-capturing device, a first image of the detection zone before injection of the saliva sample;
capturing, utilizing the image-capturing device, a second image of the detection zone after at least four minutes of interaction between the injected saliva sample and the array of chemical receptors; and
detecting a COVID-19 infection status of the person by analyzing color changes of the array of chemical receptors in the second image respective to the first image, comprising:
generating a first color value vector associated with the first image, the first color value vector comprising a first array of a respective first set of three numerical color values of three respective color components of color of each respective chemical receptor of the array of chemical receptors in the first image, the three color components comprising red, green, and blue;
generating a second color value vector associated with the second image, the second color value vector comprising a second array of a respective second set of three numerical color values respective to the three color components of color of each respective chemical receptor of the array of chemical receptors in the second image;
generating a difference color value vector by subtracting each color value of the first color value vector from a respective color value of the second color value vector;
calculating a magnitude of the difference color value vector; and
detecting the COVID-19 infection status of the person, comprising:
detecting the person being healthy responsive to the magnitude of the difference color value vector being more than 342.4; or
detecting the person being COVID-19 infected responsive to the magnitude of the difference color value vector being less than 342.4.

2. A system for detecting COVID-19 infection, comprising:
a colorimetric sensor, comprising:
a detection zone, comprising an array of chemical receptors deposited on a respective array of individual areas of a hydrophilic paper, the array of chemical receptors configured to interact with a saliva sample acquired from a person, the person being suspected to be infected by COVID-19 virus, the array of chemical receptors comprising:
an array of functionalized nanoparticles, comprising three aqueous solutions of three distinctive functionalized gold nanoparticles (AuNPs) with a concentration of 4.5 mg mL$^{-1}$, the three distinctive functionalized AuNPs comprising:
AuNPs functionalized with bovine serum albumin (BSA) (BSA-AuNPs);
AuNPs functionalized with caffeic acid (CA) (CA-AuNPs); and
AuNPs functionalized with poly glutamic acid (PGA) (PGA-AuNPs);
an array of pH-sensitive organic dyes comprising three distinctive solutions of three respective distinctive mixtures of a pH- sensitive organic dye and an additive with a volume ratio of pH- sensitive organic dye:additive equal to 3:1, the three distinctive mixtures of the pH-sensitive organic dye and the additive comprising:
a mixture of bromophenol red and DWES, the DWES comprising a mixture of 2,4-dinitrophenylhydrazine, deionized water, Ethanol (EtOH), and $H_2SO_4$;
a mixture of bromocresol purple and DWES; and
a mixture of bromophenol red and phenylboronic acid (PBA);
an array of three solutions of three respective distinctive porphyrin-based dyes with a concentration of 4.5 mg mL$^{-1}$ in ethanol, the three distinctive porphyrin-based dyes comprising:
[meso-tetraphenylporphyrin]Iron(III) chloride (Fe(III)TPPCl);
[meso-tetraphenylporphyrin]-Tin (II) (Sn(II)TPP); and
meso-tetrakis(4-hydroxyphenyl) porphyrin-manganese (III) acetate (Mn(III)T(4-OH)PP(OAc)); and
an array of three solutions of three respective distinctive metal ion complexes with a concentration of 0.05 mol L$^{-1}$ in a borate buffer solution with pH value of 9.0, the three distinctive metal ion complexes comprising:
a complex of pyrocatechol violet (Py) with V (IV) ions;
a complex of Py with Fe (II) ions; and
a complex of Py with Cu (II) ions;
an injection zone configured to inject the saliva sample thereon, the injection zone comprising a bare part of the hydrophilic paper covering the array of chemical receptors, the hydrophilic paper folded along a line between the injection zone and detection zone, the injection zone configured to allow the injected saliva to penetrate to the array of chemical receptors; and
a hydrophobic barrier, comprising a hydrophobic material filled within texture of the hydrophilic paper except the injection zone and the array of individual areas, the hydrophobic barrier configured to prevent spillover of the saliva sample from a first individual area of the array of individual areas to a second individual area of the array of individual areas;

an image-capturing device, configured to capture an image of the detection zone; and a processing unit electrically connected to the image-capturing device, the processing unit comprising:
  a memory having processor-readable instructions stored therein; and
  a processor configured to access the memory and execute the processor-readable instructions, which, when executed by the processor configures the processor to perform a method, the method comprising:
    capturing, utilizing the image-capturing device, a first image of the detection zone before injection of the saliva sample;
    capturing, utilizing the image-capturing device, a second image of the detection zone after at least four minutes of interaction between the injected saliva sample and the array of chemical receptors; and
    detecting a COVID-19 infection status of the person by analyzing color changes of the array of chemical receptors in the second image respective to the first image.

3. The system of claim 2, wherein analyzing color changes of the array of chemical receptors in the second image respective to the first image comprises:
  generating a first color value vector associated with the first image, the first color value vector comprising a first array of a respective first set of three numerical color values of three respective color components of color of each respective chemical receptor of the array of chemical receptors in the first image, the three color components comprising red, green, and blue;
  generating a second color value vector associated with the second image, the second color value vector comprising a second array of a respective second set of three numerical color values respective to the three color components of color of each respective chemical receptor of the array of chemical receptors in the second image;
  generating a difference color value vector associated with the saliva sample by subtracting each color value of the first color value vector from a respective color value of the second color value vector; and
  detecting the COVID-19 infection status of the person based on the difference color value vector.

4. The system of claim 3, wherein each of the first color value vector and the second color value vector is defined by:

$$V_j=[R_{1j}G_{1j}B_{ij} \ldots R_{ij}G_{ij}B_{ij} \ldots R_{nj}G_{nj}B_{nj}],$$

wherein:
  j is equal to 1 for the first image and 2 for the second image;
  $R_{ij}$ comprises red component value of color of $i^{th}$ chemical receptor of the array of chemical receptors in the $j^{th}$ image;
  $G_{ij}$ comprises green component value of color of $i^{th}$ chemical receptor of the array of chemical receptors in the $j^{th}$ image;
  $B_{ij}$ comprises blue component value of color of $i^{th}$ chemical receptor of the array of chemical receptors in the $j^{th}$ image; and n comprises total number of chemical receptors of the array of chemical receptors.

5. The system of claim 4, wherein the difference color value vector is defined by:

$$\Delta V=[\Delta R_1 \Delta G_1 \Delta B_1 \ldots \Delta R_i \Delta G_i \Delta B_i \ldots \Delta R_n \Delta G_n \Delta B_n],$$

wherein:
  $\Delta R_i$ is defined by a relation of $\Delta R_i=R_{i2}-R_{i1}$;
  $\Delta G_i$ is defined by a relation of $\Delta G_i=G_{i2}-G_{i1}$; and
  $\Delta B_i$ is defined by a relation of $\Delta B_i=B_{i2}-B_{i1}$.

6. The system of claim 5, wherein detecting the COVID-19 infection status of the person based on the difference color value vector comprises:
  calculating a magnitude of the difference color value vector using a relation defined by:

$$|\Delta V|=\sqrt{\Sigma_{i=1}^{n}(\Delta R_i)^2+(\Delta G_i)^2+(\Delta B_i)^2},$$

wherein $|\Delta V|$ is the magnitude of the difference color value vector; and detecting the COVID-19 infection status of the person, comprising:
  detecting the person being healthy responsive to the magnitude of the difference color value vector being more than a threshold value; or
  detecting the person being COVID-19 infected responsive to the magnitude of the difference color value vector being less than the threshold value.

7. The system of claim 6, wherein the threshold value comprises a value of 342.4.

8. The system of claim 5, wherein detecting the COVID-19 infection status of the person based on the difference color value vector comprises:
  comparing each element of the difference color value vector with a respective element of three reference difference color value vectors,
  comparing each element of the difference color value vector with a respective element of three reference difference color value vectors, each of the three difference color value vectors comprising a different one of:
    a first mean difference color value vector of a first plurality of difference color value vectors generated for a first respective plurality of saliva samples acquired from a respective plurality of COVID-19 patients;
    a second mean difference color value vector of a second plurality of difference color value vectors generated for a second respective plurality of saliva samples acquired from a respective plurality of healthy individuals; and
    a third mean difference color value vector of a third plurality of difference color value vectors generated for a third respective plurality of saliva samples acquired from a respective plurality of cured individuals after a COVID-19 infection; and
  detecting the person being one of a COVID-19 infected patient, a healthy individual, or a cured individual after a COVID-19 infection, comprising:
    detecting the person being infected by COVID-19 virus responsive to a difference percentage between each element of the difference color value vector and the respective element of the first reference difference color value vector being less than 5%;
    detecting the person being healthy responsive to a difference percentage between each element of the difference color value vector and the respective element of the second reference difference color value vector being less than 5%; or detecting the person being cured after a COVID-19 infection responsive to a difference percentage between each element of the difference color value vector and the respective element of the third reference difference color value vector being less than 5%.

9. The system of claim 8, wherein the method further comprises generating the three reference difference color value vectors, comprising:
generating three pluralities of difference color value vectors associated with three respective pluralities of saliva samples acquired from three respective groups, the three groups comprising:
a plurality of COVID-19 patients;
a plurality of healthy individuals; and
a plurality of cured individuals after a COVID-19 infection; and
forming a respective reference difference color value vector for each plurality of difference color value vectors of three pluralities of difference color value vectors by calculating an average of respective elements of each plurality of difference color value vectors.

10. The system of claim 2, wherein detecting the COVID-19 infection status of the person comprises detecting the person being infected by COVID-19 virus responsive to detecting a change in color of at least two COVID-19 indicative chemical receptors in the second image respective to the first image, the at least two COVID-19 indicative chemical receptors comprising:
a first pH-sensitive organic dye, comprising the mixture of bromophenol red and DWES with the volume ratio of bromophenol red: DWES equal to 3:1; and
a second pH-sensitive organic dye, comprising the mixture of bromocresol purple and DWES in ethanol with the volume ratio of bromophenol purple: DWES equal to 3:1.

11. The system of claim 10, wherein detecting the COVID-19 infection status of the person further comprises detecting a severity grade of COVID-19 infection of the person, comprising:
extracting two sets of three numerical color values of the second pH-sensitive organic dye in the first image and the second image, the three numerical color values comprising respective values of three color components of color of the second pH-sensitive organic dye, the three color components comprising red, green, and blue, extracting the two sets comprising extracting a first set associated with the first image and extracting a second set associated with the second image;
generating a difference color value vector associated with the second pH-sensitive organic dye by subtracting the two sets of three numerical color values from each other;
calculating a magnitude of discoloration of the second pH-sensitive organic dye in the second image respective to the first image by calculating magnitude of the difference color value vector associated with the second pH-sensitive organic dye defined by:

$$|\Delta V| = \sqrt{(\Delta R)^2 + (\Delta G)^2 + (\Delta B)^2},$$

wherein:
$|\Delta V|$ is the magnitude of discoloration of the second pH-sensitive organic dye;
$\Delta R$ is a difference between red color values in the first image and the second image;
$\Delta G$ is a difference between green color values in the first image and the second image; and
$\Delta B$ is a difference between blue color values in the first image and the second image; and
detecting the severity grade of COVID-19 infection of the person, comprising:
detecting the person being mild infected by COVID-19 virus if the magnitude of discoloration of the second pH-sensitive organic dye is in a range of 0 to 150, a mild infection by COVID-19 virus being determined as a status corresponding to a cycle threshold (CT) number for N gene obtained in a polymerase-chain-reaction (PCR) test applied to the person utilizing a PCR test tool being in a range of 28 to 32;
detecting the person being moderately infected by COVID-19 virus if the magnitude of discoloration of the second pH-sensitive organic dye being in a range of 150 to 160, a moderate infection by COVID-19 virus being determined as a status corresponding to the CT number being in a range of 23 to 27;
detecting the person being severely infected by COVID-19 virus if the magnitude of discoloration of the second pH-sensitive organic dye being in a range of 160 to 180, a severe infection by COVID-19 virus being determined as a status corresponding to the CT number being in a range of 18 to 22; and
detecting the person being highly-severe infected by COVID-19 virus if the the magnitude of discoloration of the second pH-sensitive organic dye being in a range of 180 to 220, a highly-severe infection by COVID-19 virus comprising the CT number being in a range of 15 to 17.

* * * * *